US011299850B2

(12) United States Patent
Foody et al.

(10) Patent No.: US 11,299,850 B2
(45) Date of Patent: *Apr. 12, 2022

(54) CONVERTING LIGNOCELLULOSIC BIOMASS TO GLUCOSE USING A LOW TEMPERATURE SULFUR DIOXIDE PRETREATMENT

(71) Applicant: Iogen Corporation, Ottawa (CA)

(72) Inventors: Brian Foody, Ottawa (CA); Jeffrey S. Tolan, Ottawa (CA); Daniel G. MacDonald, Orleans (CA); Kristin Martens, Nepean (CA); Natacha Leduc, Hammond (CA); Douglas A. MacKenzie, Ottawa (CA)

(73) Assignee: Iogen Corporation, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/761,180

(22) PCT Filed: Nov. 9, 2018

(86) PCT No.: PCT/CA2018/000213
§ 371 (c)(1),
(2) Date: May 1, 2020

(87) PCT Pub. No.: WO2019/090413
PCT Pub. Date: May 16, 2019

(65) Prior Publication Data
US 2020/0354891 A1 Nov. 12, 2020

Related U.S. Application Data

(60) Provisional application No. 62/583,705, filed on Nov. 9, 2017.

(51) Int. Cl.
*D21C 1/04* (2006.01)
*C08H 8/00* (2010.01)
*C12P 7/10* (2006.01)
*C12P 19/02* (2006.01)
*C12P 19/14* (2006.01)

(52) U.S. Cl.
CPC .............. *D21C 1/04* (2013.01); *C08H 8/00* (2013.01); *C12P 7/10* (2013.01); *C12P 19/02* (2013.01); *C12P 19/14* (2013.01); *C12P 2201/00* (2013.01)

(58) Field of Classification Search
None
See application file for complete search history.

(56) References Cited

U.S. PATENT DOCUMENTS

| 2,060,068 | A | 11/1936 | Groombridge et al. |
|---|---|---|---|
| 2,418,167 | A | 4/1947 | Du Bois |
| 2,710,254 | A | 6/1955 | Van Blaricom et al. |
| 2,710,255 | A | 6/1955 | Van Blaricom et al. |
| 3,046,182 | A | 11/1956 | Tomlinson et al. |
| 3,148,177 | A | 9/1964 | Wiley et al. |
| 3,251,820 | A | 5/1966 | Grangaard |
| 3,297,676 | A | 1/1967 | Brauns |
| 4,295,929 | A | 10/1981 | Leithem |
| 4,336,189 | A | 6/1982 | Hamala et al. |
| 4,461,648 | A | 7/1984 | Foody |
| 4,631,129 | A | 12/1986 | Heikkila |
| 4,988,799 | A * | 1/1991 | Samson ............... A61K 31/715 530/505 |
| 5,096,540 | A | 3/1992 | Sell et al. |
| 5,424,417 | A | 6/1995 | Torget et al. |
| 5,637,225 | A | 6/1997 | Heikkila et al. |
| 5,777,086 | A | 7/1998 | Klyosov et al. |
| 5,789,210 | A | 8/1998 | Ho et al. |
| 5,866,382 | A | 2/1999 | Hallborn et al. |
| 6,475,768 | B1 | 11/2002 | Otero et al. |
| 6,582,944 | B1 | 6/2003 | Hallborn et al. |
| 7,198,925 | B2 | 4/2007 | Foody |
| 7,527,927 | B1 | 5/2009 | Ho et al. |
| 7,527,951 | B2 | 5/2009 | Londesborough et al. |
| 7,585,652 | B2 | 9/2009 | Foody et al. |
| 7,622,284 | B2 | 11/2009 | Op Den Camp et al. |
| 7,709,042 | B2 | 5/2010 | Foody et al. |
| 7,754,456 | B2 | 7/2010 | Penttila et al. |
| 7,754,457 | B2 | 7/2010 | Foody et al. |

(Continued)

FOREIGN PATENT DOCUMENTS

EP 0450430 B1 10/1991
EP 0715657 B1 6/1996

(Continued)

OTHER PUBLICATIONS

Auxenfans et al., "Understanding the structural and chemical changes of plant biomass following steam explosion pretreatment," Biotechnol. Biofuels, 2017, vol. 10, No. 36.
Balan, V., "Current Challenges in Commercially Producing Biofuels from Lignocellulosic Biomass" ISRN Biotechnology, 2014, Article No. 463074.
Behera et al., "Importance of chemical pretreatment for bioconversion of lignocellulosic biomass" 2014, Renewable and Sustainable Energy Reviews, pp. 91-106, vol. 36.
Benjamin et al., "A General Description of Commercial Wood Pulping and Bleaching Processes", Journal of the Air Pollution Control Association, 1969, pp. 155-161 vol. 19, No. 3.

(Continued)

*Primary Examiner* — Christian L Fronda
(74) *Attorney, Agent, or Firm* — Knobbe, Martens, Olson & Bear, LLP

(57) ABSTRACT

A process for converting lignocellulosic biomass to glucose or ethanol includes subjecting the lignocellulosic biomass to a $SO_2$ pretreatment within the temperature range 110° C.-150° C. Good glucose yields have been achieved when the $SO_2$ pretreatment is conducted for more than 90 minutes and when the total amount of $SO_2$ available is greater than 20 wt % based on dry weight of lignocellulosic biomass.

21 Claims, 10 Drawing Sheets

(56) References Cited

U.S. PATENT DOCUMENTS

| | | | |
|---|---|---|---|
| 7,901,511 | B2 | 3/2011 | Griffin et al. |
| 7,993,463 | B2 | 8/2011 | Griffin et al. |
| 8,017,361 | B2 | 9/2011 | Scott et al. |
| 8,017,820 | B2 | 9/2011 | Foody et al. |
| 8,038,842 | B2 | 10/2011 | Retsina et al. |
| 8,252,568 | B2 | 8/2012 | Foody et al. |
| 8,268,125 | B2 | 9/2012 | Retsina et al. |
| 8,328,947 | B2 | 12/2012 | Anand et al. |
| 8,409,836 | B2 | 4/2013 | Vehmaanpera et al. |
| 8,603,789 | B2 | 12/2013 | Harlick |
| 8,709,770 | B2 | 4/2014 | Harlick et al. |
| 8,728,243 | B2 | 5/2014 | Van Der Meulen et al. |
| 8,815,499 | B2 | 8/2014 | Alriksson et al. |
| 8,815,561 | B2 | 8/2014 | Liu et al. |
| 8,834,633 | B2 | 9/2014 | Van Der Meulen et al. |
| 8,835,156 | B2 | 9/2014 | Bjornsson et al. |
| 8,853,478 | B2 | 10/2014 | Machhammer et al. |
| 8,871,475 | B2 | 10/2014 | Alriksson et al. |
| 8,993,274 | B2 | 3/2015 | Romero |
| 9,012,188 | B2 | 4/2015 | Van Heiningen et al. |
| 9,068,236 | B2 | 6/2015 | Heikkila et al. |
| 9,074,231 | B2 | 7/2015 | Zhu |
| 9,090,915 | B2 | 7/2015 | Wang et al. |
| 9,102,951 | B2 | 8/2015 | Griffin et al. |
| 9,212,401 | B2 | 12/2015 | Weider et al. |
| 9,243,364 | B2 | 1/2016 | Zhu et al. |
| 9,284,382 | B2 | 3/2016 | Chen et al. |
| 9,290,821 | B2 | 3/2016 | Blackbourn et al. |
| 9,303,253 | B2 | 4/2016 | Van Maris et al. |
| 9,399,840 | B2 | 7/2016 | Nelson et al. |
| 9,434,961 | B2 | 9/2016 | Dottori et al. |
| 9,624,436 | B2 | 1/2017 | Hamilton et al. |
| 9,574,212 | B2 * | 2/2017 | Foody .................. C12P 7/14 |
| 9,631,316 | B2 | 4/2017 | Retsina et al. |
| 9,738,729 | B2 | 8/2017 | Retsina et al. |
| 9,783,565 | B2 | 10/2017 | Carlius et al. |
| 9,856,605 | B2 | 1/2018 | Retsina |
| 9,873,665 | B2 | 1/2018 | Blackbourn et al. |
| 10,144,939 | B2 | 12/2018 | Noodam et al. |
| 10,316,336 | B2 | 6/2019 | Survase et al. |
| 10,421,667 | B2 * | 9/2019 | Foody .................. C12P 7/16 |
| 10,513,714 | B2 | 12/2019 | Foody et al. |
| 10,513,715 | B2 * | 12/2019 | Foody .................. C12P 7/54 |
| 10,655,149 | B2 * | 5/2020 | Dechman ............... C12P 19/14 |
| 10,662,455 | B2 * | 5/2020 | Tolan .................. C13K 13/002 |
| 10,995,314 | B2 * | 5/2021 | Foody .................. D21C 1/04 |
| 11,008,598 | B2 * | 5/2021 | Foody .................. C12P 7/10 |
| 2007/0254348 | A1 | 9/2007 | Retsina et al. |
| 2009/0118477 | A1 | 5/2009 | Hallberg et al. |
| 2010/0056774 | A1 | 3/2010 | Anand et al. |
| 2010/0279361 | A1 | 11/2010 | South et al. |
| 2011/0165643 | A1 | 7/2011 | Retsina et al. |
| 2011/0207922 | A1 | 8/2011 | Kubo et al. |
| 2011/0250638 | A1 * | 10/2011 | Sjoede .................. D21C 1/04 435/68.1 |
| 2011/0300586 | A1 | 12/2011 | Liu et al. |
| 2012/0041186 | A1 | 2/2012 | Pschorn et al. |
| 2012/0073199 | A1 | 3/2012 | Lewis |
| 2012/0315674 | A1 | 12/2012 | Realff et al. |
| 2013/0071903 | A1 | 3/2013 | Rowland et al. |
| 2013/0118483 | A1 | 5/2013 | Gao et al. |
| 2014/0024093 | A1 | 1/2014 | Blackbourn et al. |
| 2014/0034047 | A1 | 2/2014 | Retsina et al. |
| 2014/0053827 | A1 | 2/2014 | Macedo Baudel et al. |
| 2014/0142351 | A1 | 5/2014 | Johnston et al. |
| 2014/0154746 | A1 | 6/2014 | Jonsson et al. |
| 2014/0163210 | A1 | 6/2014 | Retsina et al. |
| 2014/0178944 | A1 | 6/2014 | Parekh et al. |
| 2014/0182582 | A1 | 7/2014 | Retsina et al. |
| 2014/0186899 | A1 | 7/2014 | Retsina et al. |
| 2014/0186901 | A1 | 7/2014 | Retsina et al. |
| 2014/0186903 | A1 | 7/2014 | Retsina et al. |
| 2015/0047629 | A1 | 2/2015 | Borden et al. |
| 2015/0225756 | A1 | 8/2015 | Retsina et al. |
| 2015/0259709 | A1 | 9/2015 | Retsina et al. |
| 2015/0299738 | A1 | 10/2015 | Wang et al. |
| 2015/0299739 | A1 | 10/2015 | Harlick et al. |
| 2016/0152779 | A1 | 6/2016 | Pylkkanen et al. |
| 2016/0237102 | A1 | 8/2016 | Retsina et al. |
| 2016/0237173 | A1 | 8/2016 | Nelson et al. |
| 2016/0257979 | A1 * | 9/2016 | Retsina .................. C12P 19/02 |
| 2016/0281298 | A1 | 9/2016 | Nelson et al. |
| 2017/0002387 | A1 | 1/2017 | Retsina et al. |
| 2017/0211231 | A1 | 7/2017 | Baker et al. |
| 2018/0016607 | A1 | 1/2018 | Hagglund |
| 2018/0037862 | A1 | 2/2018 | Foody et al. |
| 2018/0037863 | A1 | 2/2018 | Foody et al. |
| 2018/0037915 | A1 | 2/2018 | Foody et al. |
| 2019/0127275 | A1 | 5/2019 | Andresen et al. |
| 2019/0271114 | A1 | 9/2019 | Nelson et al. |
| 2021/0010036 | A1 * | 1/2021 | Tolan .................. D21C 11/0007 |

FOREIGN PATENT DOCUMENTS

| | | |
|---|---|---|
| WO | WO 89/08165 | 9/1989 |
| WO | WO2010/078930 | 7/2010 |
| WO | WO 2013/113579 A1 | 8/2013 |
| WO | WO 2016/113221 | 7/2016 |
| WO | WO 2017/112471 A1 | 6/2017 |
| WO | WO 2019/204190 | 10/2019 |
| WO | WO 2020/093131 | 5/2020 |
| WO | WO 2020/223792 | 11/2020 |

OTHER PUBLICATIONS

Bensah, E. and Mensah, M., "Chemical Pretreatment Methods for the Production of Cellulosic Ethanol: Technologies and Innovations," International Journal of Chemical Engineering, 2013, pp. 1-21, vol. 2013.

Bhalla et al., "Improved lignocellulose conversion to biofuels with thermophilic bacteria and thermostable enzymes," Bioresource Technology, 2013, pp. 751-759, vol. 128.

Boussaid et al., "Fermentability of the Hemicellulose-Derived Sugars from Steam-Exploded Softwood (Douglas Fir)," Biotechnology and Bioengineering, 1999, pp. 284-289, vol. 64, No. 3.

Brownell, H. and Saddler, J., "Steam Pretreatment of Lignocellulosic Material for Enhanced Enzymatic Hydrolysis," Biotechnology and Bioengineering, 1987, pp. 228-235, vol. 29.

Bruijnincx et al., "Lignin Valorisation The Importance of a Full Value Chain Approach," APC, 2016.

Bu et al., "Comparative Study of Sulfite Pretreatments for Robust Enzymatic Saccharification of Corn Cob Residue," Biotechnology for Biofuels, 2012, vol. 5, No. 87.

Bura et al., "Influence of Xylan on the Enzymatic Hydrolysis of Steam-Pretreated Corn Stover and Hybrid Poplar," Biotechnol Prog, 2009, pp. 315-322, vol. 25, No. 2.

Bura et al., "Moving towards commercialization of lignocellulosic biomass to fuels to chemicals. How to deal with heterogeneous biomass?" University of Washington Biofuels and Bioproducts Laboratory, 2012.

Bura et al., "Optimization of SO2-Catalyzed Steam Pretreatment of Corn Fiber for Ethanol Production", Applied Biochemistry and Biotechnology, 2003, vol. 105-108, pp. 319-335.

Bura et al., "SO2-Catalyzed Steam Explosion of Corn Fiber for Ethanol Production," Applied Biochemistry and Biotechnology, 2002, pp. 59-72, vols. 98-100.

Carrasco et al., "SO2-catalysed steam pretreatment of quinoa stalks," J Chem Technol Biotechnol, 2015, pp. 64-71, vol. 90.

Carrasco et al., "SO2-catalyzed steam pretreatment and fermentation of enzymatically hydrolyzed sugarcane bagasse," Enzyme and Microbial Technology, 2010, pp. 64-73, vol. 46.

Carrasco, "Arabinosylated phenolics obtained from SO2-steam-pretreated sugarcane bagasse," Journal of Chemical Technology and Biotechnology, 2012, pp. 1723-1726, vol. 87.

Chacha et al., "Steam Pretreatment of Pine (Pinus patula) Wood Residue for the Production of Reducing Sugars," Cellulose Chemistry and Technology, 2011, pp. 495-501, vol. 45 (7-8).

Chandra et al., "Enhancing Hemicellulose Recovery and the Enzymatic Hydrolysis of Cellulose by Adding Lignosulfonates during

(56) References Cited

OTHER PUBLICATIONS the Two-Stage Steam Pretreatment of Poplar," ACS Sustainable Chem Eng, 2015, pp. 986-991, vol. 3.
Cheng et al., "High titer and yield ethanol production from undetoxified whole slurry of Douglas-fir forest residue using pH profiling in SPORL," Biotechnology for Biofuels, 2015, pp. 1-10, vol. 8:22.
Chum et al., "Pretreatment—Catalyst Effects and the Combined Severity Parameter," Appl. Biochem. and Biotech., 1990, vol. 24/25.
Chylenski et al., "Enzymatic degradation of sulfite-pulped softwoods and the role of LPMOs," Biotechnol. Biofuels, 2017, 10/177.
Clark et al., "Steam Explosion of the Softwood Pinus Radiata with Sulphur Dioxide Addition. II. Process Characterisation," Journal of Wood Chemistry and Technology, 1989, pp. 135-166, vol. 9:2.
Clark et al., "Steam Explosion of the Softwood Pinus Radiata with Sulphur Dioxide Addition. I. Process Optimization," Journal of Wood Chemistry and Technology, 1987, pp. 373-403, vol. 7:3.
Corrales et al., "Structural evaluation of sugar cane bagasse steam pretreated in the presence of $CO_2$ and $SO_2$," Biotechnology for Biofuels, 2012, pp. 1-8, vol. 5:36.
De Bari et al., "$SO_2$-Catalyzed Steam Fractionation of Aspen Chips for Bioethanol Production: Optimization of the Catalyst Impregnation," Ind. Eng. Chem. Res, 2007, pp. 7711-7720, vol. 46.
Dekker, R.F.H. et al., "Enzymic Saccharification of Sugarcane Bagasse Pretreated by Autohydrolysis-Steam Explosion," Biotechnology and Bioengineering, 1983, pp. 3027-3048, vol. XXV.
Dekker, Robert F. H., "The Utilization of Autohydrolysis-Exploded Hardwood (Eucalyptus Regnans) and Softwood (Pinus Radiata) Sawdust for the Production of Cellulolytic Enzymes and Fermentable Substrates," Biocatalysis, 1987, pp. 63-75, vol. 1.
Deshpande et al., "The reactivity of lignin carbohydrate complex (LCC) during manufacture of dissolving pulp from softwood," Industrial Crops & Products, 2018, pp. 315-322, vol. 115.
Deshpande et al., "The influence of Different Types of Bisulfite Cooking Liquors on Pine Wood Components," BioResources, 2016, pp. 5961-5973, vol. 11. No. 3.
Deshpande, R., "The initial phase of sodium sulfite pulping of softwood", Doctoral Thesis, Karlstad University Studies, 2016.
Ehsanipour, Mandana, "Bioconversion of lignocellulosic hydrolysate to acetic acid using Moorella thermoacetica," a thesis submitted in partial fulfillment of the requirements for the degree of Master of Science at University of Washington, 2015.
Eklund et al., "The Influence of $SO_2$ and $H_2SO_4$ Impregnation of Willow Prior to Steam Pretreatment," 1995, Bioresource Engineering, pp. 225-229, vol. 52.
Elander et al., "Summary of findings from the Biomass Refining Consortium for Applied Fundamentals and Innovation (CAFI): corn stover pretreatment," 2009, Cellulose, pp. 649-659, vol. 16.
Ewanick et al., "The effect of biomass moisture content on bioethanol yields from steam pretreated switchgrass and sugarcane bagasse," 2011, Bioresource Technology, pp. 2651-2658, vol. 102.
Fan et al., "Optimization of $SO_2$-catalyzed hydrolysis of corncob for xylose and xylitol production," 2014, J Chem Technol Biotechnol, pp. 1720-1726, vol. 89.
Fatehi et al., "Extraction of Technical Lignins from Pulping Spent Liquors, Challenges and Opportunities," Chapter 2 Production of Biofuels and Chemicals from Lignin, 2016, pp. 35-54.
Felby et al., "Ethanol from Wheat Straw Cellulose by Wet Oxidation Pretreatment and Simultaneous Saccharification and Fermentation", American Chemical Society, ACS Symposium Series, 2003, pp. 157-174.
Frolander, et al., "Conversion of cellulose, hemicellulose and lignin into platform molecules: biotechnological approach," Eurobioref. 2011.
Galbe et al., "A review of the production of ethanol from softwood," 2002, Appl Microbial Biotechnol, pp. 618-628, vol. 59.
Gao et al., "Lignin triggers irreversible cellulase loss during pretreated lignocellulosic biomass saccharification," Biotechnology for Biofuels, 2014, vol. 14, No. 175.

Gao et al., "Saccharification of recalcitrant biomass and integration options for lignocellulosic sugars from Catchlight Energy's sugar process (CLE Sugar)," Biotechnology for Biofuels, 2013, vol. 6, No. 10.
Garlock et al., "Comparative material balances around pretreatment technologies for the conversion of switchgrass to soluble sugars," 2011, Bioresource Technology, pp. 11063-11071, vol. 102.
Gelosia et al., "Fractionation of Lignocellulosic Residues Coupling Steam Explosion and Organosolv Treatments Using Green Solvent Valerolactone," Energies, 2017, vol. 10.
Gregg et al., "A Techno-Economic Assessment of the Pretreatment and Fractionism Steps of a Biomass-to-Ethanol Process," 1996, Applied Biochemistry and Biotechnology, pp. 711-727, vol. 57/58.
Gu et al., "Fermentative High-Titer Ethanol Production from Douglas-Fir Forest Residue Without Detoxification Using SPORL: High $SO_2$ Loading at Low Temperature," 2016, Industrial Biotechnology, pp. 168-175, vol. 12, No. 3.
Harris et al., "Stimulation of Lignocellulosic Biomass Hydrolysis by Proteins of Glycoside Hydrolase Family 61: Structure and Function of a Large, Enigmatic Family," 2010, Biochemistry, pp. 3305-3316, vol. 49.
Hodge et al., "Soluble and insoluble solids contributions to high-solids enzymatic hydrolysis of lignocellulose," 2008, Bioresource Technology, pp. 8940-8948, vol. 99.
Huang et al., "Novel process for the coproduction of xylo-oligosaccharides, fermentable sugars, and lignosulfonates from hardwood," Bioresource Technology, 2016, pp. 600-607, vol. 219.
Iakovlev et al., "Kinetics of fractionation by $SO_2$-ethanol-water (SEW) treatment: understanding the deconstruction of spruce wood chips," RSC Advances, 2012, pp. 3057-3068, vol. 2, No. 7.
Iakovlev et al., "$SO_2$-ethanol-water (SEW) fractionation process: Production of dissolving pulp from spruce," Cellulose, 2014, pp. 1419-1429, vol. 21.
Karimi et al., "A critical review of analytical methods in pretreatment of lignocelluloses: Composition, imaging, and crystallinity," Bioresource Technology, 2016, pp. 1008-1018, vol. 200.
Keller et al., "Magnesium Bisulfite Pulping and Papermaking with Southern Pine," US Forest Service Research Paper, 1967.
Kilian, A., "Control of an acid sulphite batch pulp digester based on a fundamental process model,", Master Thesis, 1999, University of Pretoria.
Kumar et al., "Access of Cellulase to Cellulose and Lignin for Poplar Solids Produced by Leading Pretreatment Technologies," 2009, Biotechnol. Prog., pp. 807-819, vol. 25, No. 3.
Kumar et al., "Effects of Cellulase and Xylanase Enzymes on the Deconstruction of Solids from Pretreatment of Poplar by Leading Technologies," Biotechnol. Prog., 2009, pp. 302-314, vol. 25, No. 2.
Kumar et al., "Recent updates on different methods of pretreatment of lignocellulosic feedstocks: a review," Bioresour Bioprocess, 2017, vol. 4., No. 7.
Lan et al., "High titer ethanol production from SPORL-pretreated lodgepole pine by simultaneous enzymatic saccharification and combined fermentation," 2013, Bioresource Technology, pp. 291-297, vol. 127.
Leu et al., "Substrate-Related Factors Affecting Enzymatic Saccharification of Lignocelluloses; Our Recent Understanding," 2013, Bioenerg. Res., pp. 405-415, vol. 6.
Liu et al., "Multistep Process to Produce Fermentable Sugars and Lignosulfonates from Softwood Enzymolysis Residues," ACS Sustainable Chem. Eng., 2016, pp. 7225-7230, vol. 4.
Liu et al., "Effect of Sulfite Pretreatment to Overcome the Recalcitrance of Lignin (SPORL) on Enzymatic Saccharification of Corn Stalk," 2011, Biosouces, 5001-5011, vol. 6(4).
Llano et al., "Detoxification of a Lignocellulosic Waste from a Pulp Mill to Enhance Its Fermentation Prospects", Energies, 2017, vol. 10, No. 348.
Mackie et al., "Effect of Sulphur Dioxide and Sulphuric Acid on Steam Explosion of Aspenwood," 1985, Journal of Wood Chemistry and Technology, pp. 405-425, vol. 5(3).
Mamers et al., "Explosion pretreatment of Pinus radiata woodchips for the production of fermentation substrates," 1984, Apita, pp. 644-649, vol. 37, No. 8.

(56) References Cited

OTHER PUBLICATIONS

Martin et al., "Comparison of the Fermentability of Enzymatic Hydrolyzates of Sugarcane Bagasse Pretreated by Steam Explosion Using Different Impregnating Agents," 2002, Applied Biochemistry and Biotechnology, pp. 699-716, vol. 98-100.
Miles-Barrett et al., "Use of Bisulfite Processing to Generate Hight BO4 Content Water Soluble Lignosulfonates," ACS Sustainable Chem. Eng., 2017, pp. 1831-1839, vol. 5.
Monavari et al., "Improved One-Step Steam Pretreatment if SO2-Impregnated Softwood with Time-Dependant Temperature Profile for Ethanol Production," 2010, Biotechnol. Prog., pp. 1054-1060, Vol.
Mupondwa et al., "Status of Canada's lignocellulosic ethanol: Part I: Pretreatment technologies," Renewable and Sustainable Energy Reviews, 2017, pp. 178-190, vol. 72.
Nguyen et al., "Dilute Acid Pretreatment of Softwoods," 1998, Applied Biochemistry and Biotechnology, pp. 77-89, vol. 70-72.
Nguyen et al., "Two-Stage Dilute Acid Pretreatment of Softwoods," 2000, Applied Biochemistry and Biotechnology, 561-576, vol. 84-86.
Nrel, "Continual Shrinking-Bed Reactor Boosts Biomass Ethanol," Research Brief.
Ohgren et al., "Optimization of Steam Pretreatment of SO2-Impregnated Corn Stover for Fuel Ethanol Production," 2005, Applied Biochemistry and Biotechnology, pp. 1055-1067, vol. 121-124.
Pan et al., "Woody Biomass Sulfite Pretreatment to Overcome Lignocellulose Recalcitrance for Biofuel Production", Wisconsin Alumni Research Foundation.
Paulova et al., "Production of 2nd Generation of Liquid Biofuels", Liquid Gaseous and Solid Biofuels-Conversion Techniques, 2013.
Pedersen et al., "Low temperature lignocellulose pretreatment: effects and interactions of pretreatment pH are critical for maximizing enzymatic monosaccharide yields from wheat straw," 2011, Biotechnology for Biofuels, pp. 1-10, vol. 4:11.
Rakkolainen et al., "SO2-Ethanol-Water Fractionation of Forest Biomass and Implications for Biofuel Production by Abe Fermentation," 2010, Cellulose Chem. Technol., pp. 139-145, vol. 44.
Ramos et al., "Characterization of Residual Lignin after SO2-Catalyzed Steam Explosion and Enzymatic Hydrolysis of Eucalyptus viminalis Wood Chips," 1999, J. Agric. Food Chem., pp. 2295-2302, vol. 47.
Ramos et al., "Comparison of Steam Pretreatment of Eucalyptus, Aspen, and Spruce Wood Chips and their Enzymatic Hydrolysis," 1992, Applied Biochemistry and Biotechnology, pp. 37-48, vol. 34/35.
Ramos et al., "Effect of enzymatic hydrolysis on the morphology and fine structure of pretreated cellulosic residues," 1993, Enzyme Microb. Technol., pp. 821-831, vol. 15.
Ren et al., "Comparative Evaluation of Magnesium Bisulfite Pretreatment under Different pH Values for Enzymatic Hydrolysis of Corn Stover," Bioresources, 2016, pp. 7258-7270, vol. 11, No. 3.
Reknes, K., "The chemistry of lignosulphonate and the effect on performance of lignosulfonate base plasticizers and superplasticizers," 29th Conference on Our World in Concrete & Structures, Aug. 2004, Singapore.
Rollin et al., "Increasing Cellulose Accessibility is More Important than Removing Lignin: A Comparison of Cellulose Solvent-Based Lignocellulose Fractionation and Soaking in Aqueous Ammonia," Biotechnology and Bioengineering, 2011, pp. 22-30, vol. 108. No. 1.
Sassner et al., "Steam Pretreatment of Salix with and without SO2 Impregnation for Production of Bioethanol," 2005, Applied Biochemistry and Biotechnology, pp. 1101-1117, vol. 121-124.
Schell et al., "A Technical and Economic Analysis of Acid-Catalyzed Steam Explosion and Dilute Sulfuric Acid Pretreatments Using Wheat Straw or Aspen Wood Chips," 1991, Applied Biochemistry and Biotechnology, pp. 87-97, vol. 28/29.
Schell et al., "Pretreatment of Softwood by Acid-Catalyzed Steam Explosion Followed by Alkali Extraction," 1998, Applied Biochemistry and Biotechnology, pp. 17-24, vol. 70-72.
Schwald et al., "Assessment of Pretreatment Conditions to Obtain Fast Complete Hydrolysis on High Substrate Concentrations," 1989, Applied Biochemistry and Biotechnology, pp. 29-44, vol. 20/21.
Selig et al., "The Effect of Lignin Removal by Alkaline Peroxide Pretreatment on the Susceptibility of Corn Stover to Purified Celluloytic and Xylanolytic Enzymes," Appl. Biochem. Biotechnol., 2009, pp. 397-406, Vo. 155.
Sendelius, "Steam Pretreatment Optimisation for Sugarcane Bagasse in Bioethanol Production," 2005, Master of Science Thesis, Lund University, Sweden.
Shahzad, M. A., "Effect of temperature and time on acid sulfite cooking for dissolving pulp," Degree Project, Karlstad University, 2012.
Shevchenko et al., "Optimization of monosaccharide recovery by post-hydrolysis of the water-soluble hemicellulose component after steam explosion of softwood chips," 2000, Bioresource Technology, pp. 207-211, vol. 72.
Shevchenko et al., "The Nature of Lignin from Steam Explosion/Enzymatic Hydrolysis of Softwood," 1999, Applied Biochemistry and Biotechnology, pp. 867-876, vol. 77-79.
Shi et al., "Sugar yields from dilute sulfuric acid and sulfur dioxide pretreatments and subsequent enzymatic hydrolysis of switchgrass," 2011, Bioresource Technology, pp. 8930-8938, vol. 102.
Shi et al., "Degradation Kinetics of Monosaccharides in Hydrochloric, Sulfuric, and Sulfurous Acid," Bioresources, 2012, pp. 4085-4097, vol. 7, No. 3.
Shi et al., "Pretreatment of Lignocellulosic Biomass", Beems Module B1.
Shuai et al., "Comparative study of SPORL and dilute-acid pretreatments of spruce for cellulosic ethanol production," 2010, Bioresource Technology, pp. 3106-3114, vol. 101.
Sipos et al., "Steam pretreatment of dry and ensiled industrial hemp for ethanol production," 2010, Biomass and Bioenergy, pp. 1-11.
Sixta, H., "Conventional Acid Sulfite Pulping," Aalto University, 2015.
Sluiter et al., "Determination of Structural Carbohydrates and Lignin in Biomass," NREL Technical Report 2012.
Soderstrom et al., "Effect of Washing on Yield in One- and Two-Step Steam Pretreatment of Softwood for Production of Ethanol," 2004, Biotechnol. Prog., pp. 744-749, vol. 20.
Soderstrom et al., "Separate versus Simultaneous Saccharification and Fermentation of Two-Step Steam Pretreated Softwood for Ethanol Production," 2005, Journal of Wood Chemistry, pp. 187-202, vol. 25.
Soderstrom et al., "Two-Step Steam Pretreatment of Softwood with SO2 Impregnation for Ethanol Production," 2002, Applied Biochemistry and Biotechnology, pp. 5-21, vol. 98-100.
Stenberg et al., "Optimisation of Steam Pretreatment of SO2-Impregnated Mixed Softwoods for Ethanol Production," 1998, J. Chem. Technol. Biotechnol, pp. 299-308, vol. 71.
Sumerskii et al., "Fast track for quantitative isolation of lignosulfonates from spent sulfite liquors," RSC Advances, 2015, pp. 92732-92742, vol. 5.
Szengyel et al., "Cellulase Production of Trichoderma reesei Rut C 30 Using Steam-Pretreated Spruce," 2000, Applied Biochemistry and Biotechnology, pp. 679-691, vol. 84-86.
Takahashi et al., "Removal of Acetic Acid from Spent Sulfite Liquor Using Anion Exchange Resin for Effective Xylose Fermentation with Pichia stipitis," Bioresources, 2013, pp. 2417-2428, vol. 8, No. 2.
Tao et al., "Process and technoeconomic analysis of leading pretreatment technologies for lignocellulosic ethanol production using switchgrass," 2011, Bioresource Technology, pp. 11105-11114, vol. 102.
Tengborg et al., "Comparison of SO2 and H2SO4 Impregnation of Softwood Prior to Steam Pretreatment on Ethanol Production," 1998, Applied Biochemistry and Biotechnology, pp. 3-15, vol. 70-72.

(56) References Cited

OTHER PUBLICATIONS

Tengborg et al., "Reduced inhibition of enzymatic hydrolysis of steam-pretreated softwood," 2001, Enzyme and Microbial Technology, pp. 835-844, vol. 28.

Thompson et al., "Chemical preconversion: application of low-severity pretreatment chemistries for commoditization of lignocellulosic feedstock," Biofuels, 2013, pp. 323-340, vol. 4, No. 3.

Tian et al., "Comparisons of SPORL and Dilute Acid Pretreatments for Sugar and Ethanol Productions from Aspen," 2011, Biotechnol. Prog. pp. 419-427, vol. 27, No. 2.

Tian et al., "Robust cellulosic ethanol production from SPORL-pretreated lodgepole pine using an adapted strain *Saccharomyces cerevisiae* without detoxification," 2010, Bioresource Technology, pp. 8678-8685, vol. 101.

Tian et al., "A comparison of various lignin-extraction methods to enhance the accessibility and ease of enzymatic hydrolysis of the cellulosic component of steam-pretreated poplar," Biotechnol. Biofuels, 2017, vol. 10, No. 157.

Trajano et al., "Fundamentals of Biomass Pretreatment at Low pH," 2013, Aqueous Pretreatment of Plant Biomass for Biological and Chemical Conversion to Fuels and Chemicals, pp. 103-128.

Vera et al., "Synergistic effects of mixing hybrid poplar and wheat straw biomass for bioconversion processes," 2015, Biotechnol Biofuels, pp. 1-10, vol. 8:226.

Vermaas et al., "Mechanism of lignin inhibition of enzymatic biomass deconstruction," Biotechnol Biofuels, 2015, vol. 8, No. 217.

Von Sivers et al., "A Techno-Economical Comparison of Three Processes for the Production of Ethanol from Pine," 1995, Bioresource Technology, pp. 43-52, vol. 51.

Wang et al., "Ethanol production from poplar wood through enzymatic saccharification and fermentation by dilute acid and SPORL pretreatments," 2012, Fuel, pp. 606-614, vol. 95.

Wang et al., "Influence of lignin addition on the enzymatic digestibility of pretreated lignocellulosic biomasses," Bioresource Technology, 2015, pp. 7-12, vol. 181.

Wang et al., "Lignosulfonate and elevated pH can enhance enzymatic saccharification of lignocelluloses," 2013, Biotechnology for Biofuels, pp. 1-10, vol. 6:9.

Wang et al., "Sulfite Pretreatment to Overcome Recalcitrance of Lignocellulose (SPORL) for Robust Enzymatic Saccharification of Hardwoods," 2009, Biotechnol. Prog., pp. 1086-1093, vol. 25, No. 4.

Wayman et al., "Hydrolysis of Biomass by Sulphur Dioxide," 1984, Biomass, pp. 183-191, vol. 6.

Wayman et al., "SO2 Catalysed Prehydrolysis of Coniferous Wood for Ethanol Production," 1986, Biotechnology Letters, pp. 749-752, vol. 8, No. 10.

Wiman et al., "Cellulose accessibility determines the rate of enzymatic hydrolysis of steam-pretreated spruce," 2012, Bioresource Technology, pp. 208-215, vol. 126.

Wolfinger et al., "Modeling of the Acid Sulfite Pulping Process.—Problem Definition and Theoretical Approach for a Solution with the Main Focus on the Recovery of Cooking Chemicals," 2004, Lenzinger Berichte, pp. 35-45, vol. 83.

Wooley, Bob, "Production of 1,000 Gallons of BioJet," 2015, Presentation from 2015 Annual Meeting of Northwest Advanced Renewables Alliance (NARA).

Wyman et al., "Comparative data on effects of leading pretreatments and enzyme loadings and formulations on sugar yields from different switchgrass sources," 2011, Bioresource Technology,.

Wyman et al., "Comparative Sugar Recovery and Fermentation Data Following Pretreatment of Poplar Wood by Leading Technologies," 2009, Biotechnol. Prog., pp. 333-339, vol. 25, No. 2.

You et al., "Kinetics of SO2-ethanol-water (AVAR) fractionation of sugarcane straw," Bioresource Technology, 2016, pp. 111-119, vol. 210.

Zhang et al., "Sulfite (SPORL) pretreatment of switchgrass for enzymatic saccharification," 2013, Bioresource Technology, pp. 127-134, vol. 129.

Zhou et al., "Bioconversion of Beetle-Killed Lodgepole Pine Using SPORL: Process Scale-Up Design, Lignin Coproduct, and High Solids Fermentation without Detoxification," 2013, Industrial & Engineering Chemistry Research, pp. A-I.

Zhou et al., "Comparisons of high titer ethanol production and lignosulfonate properties by SPORL pretreatment of lodgepole pine at two temperatures," RSC Advances, 2014, pp. 27030-27038, vol. 4.

Zhou et al., "High titer ethanol and lignosulfonate production from SPORL pretreated poplar at pilot scale," Frontier in Energy Research, 2015, vol. 3.

Zhu et al., "Case studies on sugar production from underutilized woody biomass using sulfite chemistry", Tappi Journal, 2015, pp. 577-583, vol. 14, No. 9.

Zhu et al., "Ethanol production from SPORL-pretreated lodgepole pine: preliminary evaluation of mass balance and process energy efficiency," 2010, Appl Microbiol Biotechnol, pp. 1355-1365, vol. 86.

Zhu et al., "High Titer Ethanol Production from Forest Residue Using Sulfite Mill Pulping Chemistry," 2015, Presentation at 2015 TAPPI IBBC.

Zhu et al., "High titer ethanol production from simultaneous enzymatic saccharification and fermentation of aspen at high solids: A comparison between SPORL and dilute acid pretreatments," 2011, Bioresource Technology, pp. 8921-8929, vol. 102.

Zhu et al., "On Polydispersity of Plant Biomass Recalcitrance and Its Effects on Pretreatment Optimization for Sugar Production," 2011, Bioenerg. Res., pp. 201-210, vol. 4.

Zhu et al., "Quantitative predictions of bioconversion of aspen by dilute acid and SPORL pretreatments using a unified combined hydrolysis factor (CHF)," 2012, Process Biochemistry, pp. 785-791, vol. 47.

Zhu et al., "Sulfite pretreatment (SPORL) for robust enzymatic saccharification of spruce and red pine," 2009, Bioresource Technology, pp. 2411-2418, vol. 100.

Zhu et al., "Using sulfite chemistry for robust bioconversion of Douglas-fir forest residue to bioethanol at high titer and lignosulfonate: A pilot-scale evaluation," 2015, Bioresource Technology, pp. 390-397, vol. 179.

Zhu et al., "Woody biomass pretreatment for cellulosic ethanol production: Technology and energy consumption evaluation," 2010, Bioresource Technology, pp. 4992-5002, vol. 101.

International Search Report and Written Opinion dated Feb. 21, 2019 for PCT Application No. PCT/CA2018/000213, filed Nov. 9, 2018.

International Search Report and Written Opinion dated Mar. 8, 2019 for PCT Application No. PCT/CA2018/000217, filed Nov. 9, 2018.

Office Action for U.S. Appl. No. 17/040,738, dated Jun. 3, 2021 in 25 pages.

Office Action for U.S. Appl. No. 16/761,192, dated Sep. 2, 2021 in 26 pages.

Andritz, "BioFuel Equipment—derived from Pulp and Fiberboard applications for Ligno-Cellulosic BioFuel & BioChemicals Technology" 2012.

Gellerstedt et al., "Towards a new concept of lignin condensation in Kraft pulping" C.R. Biologies, 2004, vol. 327.

Gratzel et al., "Chemistry of Pulping: lignin reactions." American Chemical Society Symposium Series, 2000, vol. Ch. 20, pp. p 3932-421.

McElroy "Not so run of the Mill", Biomassmagazine, http://biomassmagazine.com/articles/1297/not-so-run-of-the-mill.

Philips, et al., "Integration of pulp and paper technology with bioethanol production", Biotechnology for Biofuels 2013 6:13.

Rodsrud et al., "History and future of world's most advanced biorefinery in operation", Biomass and Bioenergy, 2012, vol. 46, pp. 46-59.

Yan et al., "Influence of pH on the behaviour of lignosulfonate macromolecules in aqueous solution". Colloids and Surfaces: A Physiochemical and Engineering aspects, Nov. 1, 2010 (Nov. 1, 2010), vol. 37(1)pp. p. 50-58.

Zhu et al., "Applications of lignin-derived catalysts for green synthesis", Green Energy & Environment, https://doi.org/10.1016/i.gee.2019.01.003.

(56) References Cited

OTHER PUBLICATIONS

International Search Report and Written Opinion dated May 3, 2019 for PCT Application No. PCT/CA2018/000215, filed Nov. 9, 2018.

* cited by examiner

CONVERTING LIGNOCELLULOSIC BIOMASS TO GLUCOSE USING A LOW TEMPERATURE SULFUR DIOXIDE PRETREATMENT

CROSS-REFERENCE TO RELATED APPLICATIONS

This application claims the priority benefit of provisional application No. 62/583,705, filed Nov. 9, 2017, which is incorporated herein by reference.

TECHNICAL FIELD

The present disclosure relates generally to a process and/or system for converting lignocellulosic biomass to glucose or an alcohol, where the lignocellulosic biomass is pretreated with sulfur dioxide and/or sulfurous acid at low temperature prior to enzymatic hydrolysis.

BACKGROUND

Lignocellulosic biomass is an abundant organic material that can be used to produce biofuels (e.g., ethanol, butanol, methane). In many cases, the conversion of lignocellulosic biomass to biofuel involves breaking down the cellulose and hemicellulose found in lignocellulosic biomass into their corresponding monomers (e.g., sugars) so that microorganisms can use them. For example, cellulose may be broken down to glucose, whereas hemicellulose may be broken down to xylose, arabinose, mannose, galactose, and/or glucose. These sugars can then be converted to biofuel via microorganisms. For example, glucose can be fermented to produce an alcohol such as ethanol or butanol.

While lignocellulosic biomass can be broken down into sugars solely using various chemical processes (e.g., acid hydrolysis), enzymatic hydrolysis is often the preferred approach for generating glucose as it is associated with higher yields, higher selectivity, lower energy costs, and milder operating conditions. For example, the cellulose in lignocellulosic biomass may be converted to glucose by cellulases. However, as a result of the complicated structure of the plant cell wall, the enzymatic digestibility of cellulose in native lignocellulosic biomass is often low unless a large excess of enzyme is used (e.g., lignocellulosic biomass may be considered recalcitrant to biodegradation). Unfortunately, the cost of suitable enzymes can be high, and can significantly contribute to the overall costs of the process. Accordingly, it is advantageous for enzymatic hydrolysis to be preceded by a pretreatment process that makes the lignocellulosic biomass more amenable to enzymatic hydrolysis and/or reduces the amount of enzyme required.

In general, an effective pretreatment will reduce biomass recalcitrance (e.g., open up the structure of the lignocellulosic material, make the cellulose more accessible to the enzymes, and/or generally improve enzymatic digestibility of the cellulose) to an extent that enzyme loading and/or hydrolysis time is satisfactorily reduced (e.g., relative to no pretreatment). Some examples of pretreatment processes that have been used and/or proposed for preparing lignocellulosic biomass for enzymatic hydrolysis include physical pretreatment (e.g., milling and grinding), dilute acid pretreatment, alkali pretreatment (e.g., lime), ammonia fiber expansion, hot water extraction, steam explosion, organic solvent, and/or wet oxidation.

In dilute acid pretreatment, mineral acids such as $H_2SO_4$, HCl, $H_3PO_4$, or $HNO_3$, can be used to prepare the lignocellulosic biomass for enzymatic hydrolysis. Pretreating with acid under dilute conditions solubilizes the hemicellulose fraction of the lignocellulosic biomass, which can make the cellulose more accessible to the enzymes. For example, the concentration of the acid (e.g., 0.4-3%), pretreatment temperature (e.g., 140-190° C.), and/or pretreatment time (e.g., 1-40 minutes) in dilute acid pretreatment, is typically selected to maximize the amount of hemicellulose solubilized, while minimizing the amount of cellulose that is degraded.

In steam pretreatment, the lignocellulosic biomass typically is treated with high pressure saturated steam at a temperature and for a period of time selected to promote hemicellulose hydrolysis. If the pressure is quickly released, the lignocellulosic biomass undergoes an explosive decompression and the pretreatment is referred to as steam explosion. The high pressure steam modifies the plant cell wall structure, typically yielding a dark brown material from which hydrolyzed or partially hydrolyzed hemicelluloses can be recovered (e.g., by filtration and/or washing). Impregnating the lignocellulosic biomass with an acid (e.g., $H_2SO_4$, $SO_2$, oxalic acid, etc.) prior to steam pretreatment can lead to a more complete removal of hemicellulose during the steam pretreatment and/or increased enzymatic digestibility of the lignocellulosic biomass.

Some factors that can determine the efficiency of acid and/or steam pretreatment include the pretreatment time, the pretreatment temperature, and the type and concentration of acid (if used). For example, consider FIG. 1, which corresponds to FIG. 2 of U.S. Pat. No. 4,461,648 to Foody. FIG. 1 shows cellulose accessibility, as measured by the material's glucose yield in enzymatic hydrolysis, as a function of pretreatment time, for a given pretreatment temperature. More specifically, FIG. 1 shows that cellulose accessibility can increase with increasing pretreatment time up to a certain point, where it peaks. At pretreatment times past this peak, the carbohydrates in the lignocellulosic biomass can begin to degrade, thus causing the glucose yield to decrease with increasing time. The pretreatment time corresponding to maximum glucose yield (e.g., the peak in FIG. 1), is dependent, at least in part, on the pretreatment temperature (e.g., with higher pretreatment temperatures providing the same glucose yield at shorter cooking times).

Accordingly, in terms of selecting suitable pretreatment conditions, with the goal increasing glucose yield, the lower limits may be determined by temperatures and/or times that fail to modify the structure of the lignocellulosic biomass to an extent that sufficiently improves enzymatic hydrolysis, whereas the upper limits may be determined by temperatures and/or times associated with overcooking.

In addition to increasing glucose yield (i.e., by improving enzymatic digestibility of the cellulose component), it can be advantageous if the pretreatment also increases the yield of sugar products from hemicellulose (e.g., xylose). For example, since acid and/or steam pretreatment can hydrolyze or partially hydrolyze the hemicellulose component to produce a liquid fraction rich in pentose (e.g., C5 sugars such as xylose), the liquid fraction of the pretreated material can be used to increase the yield of ethanol, for xylitol production, and/or for biogas production. However, since hemicellulose generally is solubilized under conditions that are considerably milder than those required to satisfactorily reduce biomass recalcitrance, the pentose-rich liquid fraction is prone to excessive degradation. Not only does this reduce the xylose yield, but it can also produce potentially inhibitory and/or inactivating compounds. For example, xylose can degrade to form furfural.

In U.S. Pat. No. 9,434,961, there is described a process involving an acid pretreatment that allows the xylose component to be recovered more efficiently. More specifically, the pretreatment temperature is set between 130° C.-180° C., the pretreatment time is set between 30 m-4 hr, and the acid concentration is set between 0.5% and 0.9% w/w on an incoming biomass dry matter basis. Due to the use of only dilute acids, a very low loss of glucose and xylose, and hence, a very low production of potentially toxic chemicals such as furfural is reported.

However, in general, selecting the optimal pretreatment conditions can be a compromise between maximizing xylose yield, which requires relatively mild pretreatment conditions, and maximizing enzymatic cellulose digestibility, which conventionally requires more severe pretreatment conditions (e.g., at which C5 sugar loss is inevitable as a result of sugar degradation). In practice, the use of higher pretreatment temperatures and shorter pretreatment times has been found to provide a reasonable compromise between higher xylose yield and enzymatic cellulose digestibility. For example, conventional steam explosion is typically performed using temperatures in the range of 160-260° C. (e.g., 0.69-4.8 MPa), with pretreatment times between several seconds up to 30 minutes, and more commonly, using temperatures in the range of 180-220° C., for less than 10 minutes.

In order to avoid compromising between xylose yield and enzymatic cellulose digestibility, two-stage acid pretreatment processes have been proposed. In the first stage, the hemicellulose is hydrolyzed under relatively mild conditions. The material from the first stage is then filtered and/or washed to provide a xylose-rich liquid fraction and a solid fraction. The solid fraction is fed to the second stage where it is subjected to relatively harsh pretreatment conditions that improve enzymatic digestibility of the cellulose. Since the xylose-rich liquid fraction, which can be used to increase the overall sugar yield, can by-pass the second stage of pretreatment, there is less degradation of the xylose component. For example, in US Pub. No. 2012/0041186, the first stage uses a pretreatment temperature between 110° C. and 175° C., for between 10 minutes and 60 minutes, whereas the second stage uses a pretreatment temperature between 170° C. and 230° C., for between 2 minutes and 5 minutes. Notably, this approach is consistent with the general belief that steam pretreatment at temperatures below 160° C. is ineffective in terms of satisfactorily increasing enzymatic cellulose digestibility of naturally recalcitrant biomass, even when $SO_2$-catalyzed.

While a two-stage acid pretreatment potentially maximizes both glucose yield and xylose yield, it unfortunately requires two separate pretreatment reactors operating under different pretreatment conditions, and is complicated by the addition of another washing step. This additional washing step is particularly disadvantageous as it may require specialized equipment for washing at elevated temperatures, the use of hot water for washing, and/or for the washed material to be reheated for the second stage. It addition, it still relies on high temperatures to increase enzymatic cellulose digestibility of the naturally recalcitrant biomass. High temperatures typically require the generation and use of high pressure steam. It addition, high temperatures necessitate the use of equipment that can maintain and tolerate the high pressures and temperatures, and the use of equipment to bring the feed up to the necessary pressure.

SUMMARY

The present disclosure describes one or more embodiments where lignocellulosic biomass is subjected to an acid pretreatment using sulfur dioxide and/or sulfurous acid followed by enzymatic hydrolysis. Advantageously, it has been found that by conducting the pretreatment at a relatively low temperature (e.g., between 110° C. and 150° C.), while increasing the severity of the pretreatment by using a relatively long pretreatment time (e.g., more than 90 minutes) and/or a relatively high total amount of $SO_2$ (e.g., greater than 20 wt % based on dry weight of lignocellulosic biomass), both a high glucose yield and a high xylose yield can be achieved without having to heat the lignocellulosic biomass above 160° C. In other words, the need for a high-temperature, second-stage of pretreatment is avoided. Various embodiments thus provide a combination of conditions (relatively low temperature in combination with a relatively long pretreatment time and/or a relatively high total amount of $SO_2$) that is essentially opposite to the conventional combination of relatively high temperature and short treatment times at which, for example, conventional $SO_2$ steam pretreatment is typically performed.

According to one aspect of the invention there is provided a method for converting lignocellulosic biomass to glucose comprising: pretreating the lignocellulosic biomass to provide a pretreated material, said pretreating comprising subjecting the lignocellulosic biomass to a $SO_2$ pretreatment, said $SO_2$ pretreatment comprising heating said lignocellulosic biomass with at least one of sulfur dioxide and sulfurous acid, said heating conducted between 110° C. and 150° C. for more than 90 minutes, said $SO_2$ pretreatment conducted with a total amount of sulfur dioxide greater than 20 wt % based on dry weight of lignocellulosic biomass; and hydrolyzing at least 60% of the cellulose in the pretreated material to glucose, said hydrolyzing including adding enzyme to at least a solid fraction of the pretreated material, said enzyme including a cellulase.

According to one aspect of the invention there is provided a process for the production of an alcohol from lignocellulosic biomass, said process comprising: feeding the lignocellulosic biomass into a pretreatment reactor; pretreating the lignocellulosic biomass in the pretreatment reactor to provide a pretreated material, said pretreating comprising heating the lignocellulosic biomass with at least one of sulfur dioxide and sulfurous acid between 110° C. and 150° C. for more than 100 minutes, where a total amount of sulfur dioxide is greater than 20 wt % based on dry weight of lignocellulosic biomass, where alkali is added in an amount in the range from 0 to 0.5 wt % based on dry weight of incoming lignocellulosic biomass and organic solvent is added in an amount in the range from 0 to 5 wt % based on dry weight of incoming lignocellulosic biomass; hydrolyzing at least 60% of the cellulose in the lignocellulosic biomass to glucose, said hydrolyzing including adding cellulase; fermenting the glucose to produce the alcohol; and recovering the alcohol.

DETAILED DESCRIPTION

Figure 1:
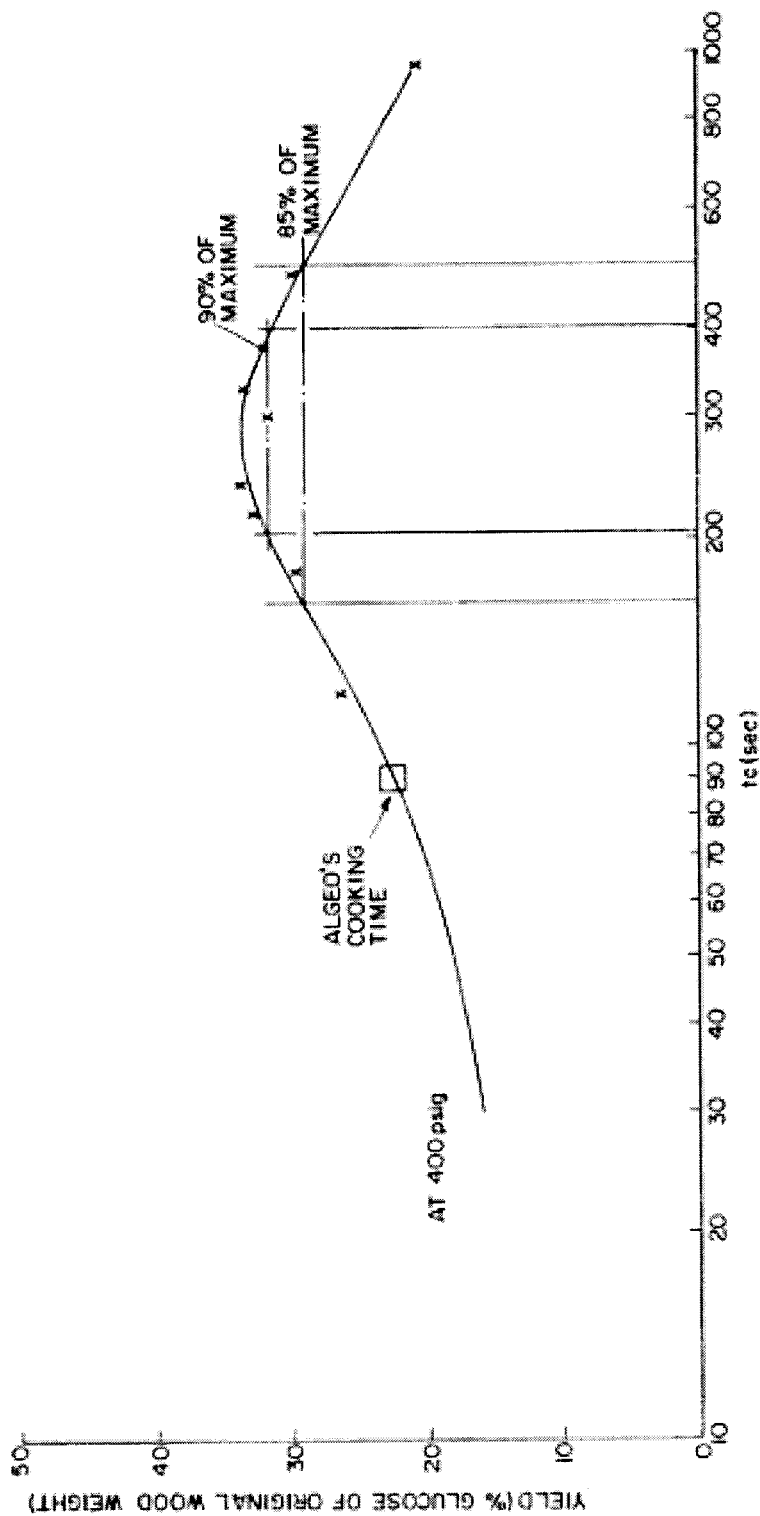
FIG. 1 is a prior art graph of glucose yield as a function of pretreatment time.

Certain exemplary embodiments of the invention now will be described in more detail, with reference to the drawings, in which like features are identified by like reference numerals. The invention may, however, be embodied in many different forms and should not be construed as limited to the embodiments set forth herein.

The terminology used herein is for the purpose of describing certain embodiments only and is not intended to be limiting of the invention. For example, as used herein, the singular forms "a", "an," and "the" may include plural references unless the context clearly dictates otherwise. The terms "comprises", "comprising", "including", and/or "includes", as used herein, are intended to mean "including but not limited to". The term "and/or", as used herein, is intended to refer to either or both of the elements so conjoined. The phrase "at least one" in reference to a list of one or more elements, is intended to refer to at least one element selected from any one or more of the elements in the list of elements, but not necessarily including at least one of each and every element specifically listed within the list of elements. Thus, as a non-limiting example, the phrase "at least one of A and B" may refer to at least one A with no B present, at least one B with no A present, or at least one A and at least one B in combination. In the context of describing the combining of components by the "addition" or "adding" of one component to another, those skilled in the art will understand that the order of addition is not critical (unless stated otherwise). Thus, for example, reference herein to "adding" an acid to a biomass will be understood as a reference to the act of combining the acid and biomass, whether by adding the acid to the biomass, adding the biomass to the acid, or both. The terms "first", "second", etc., may be used to distinguish one element from another, and these elements should not be limited by these terms. Unless defined otherwise, all technical and scientific terms used herein have the same meanings as commonly understood by one of ordinary skill in the art.

The present disclosure describes a process where lignocellulosic biomass is subjected to an acid pretreatment using sulfur dioxide ($SO_2$) and/or sulfurous acid followed by enzymatic hydrolysis. Acid pretreatments typically target hydrolysis of hemicelluloses, which is believed to open up the structure of the lignocellulosic material. However, in conventional $H_2SO_4$ pretreatment, the low pH conditions can also result in lignin condensation. The relocation and/or modification of the lignin may affect the amount of lignin that can be removed and/or may affect the enzymatic hydrolysis. For example, lignin may act both as a physical barrier, restricting cellulose accessibility, and as a cellulase non-productive binder. However, since sulfur dioxide and/or sulfurous acid promote lignin sulfonation, lignin condensation may be less of an issue in the $SO_2$ pretreatment. Sulfonation provides the lignin with a strong hydrophilic structure, which can be dissolved more readily. In addition, sulfonated lignin (e.g., lignosulfonates, including lignosulfonic acid and its salts) may be generally advantageous for the process. For example, in U.S. Pat. No. 9,574,212, it was demonstrated that $SO_2$ pretreatment of wheat straw at 195° C. reduced the amount of enzyme required for hydrolysis relative to $H_2SO_4$ pretreatment at 200° C., even when the lignocellulosic biomass is not washed prior to hydrolysis.

Surprisingly, it has been found that the glucose yield achieved with the low temperature $SO_2$ pretreatment (e.g., between 110° C. and 150° C.) can be similar to that obtained from a $SO_2$ pretreatment at 230° C., but without the expense and/or complications associated with using high temperatures. Furthermore, it has been found that low temperature $SO_2$ pretreatment (e.g., between 110° C. and 150° C.) can reduce the amount of enzyme required by more than 75% relative to low temperature $H_2SO_4$ pretreatment. Since the cost of enzyme(s) has been regarded as one of the key hurdles towards economic viability of cellulosic ethanol production, the present disclosure can provide a better process for the commercial production of ethanol.

Moreover, it has been found that the xylose yield achieved with the low temperature $SO_2$ pretreatment (e.g., between 110° C. and 150° C.) can be high, even when the total amount of sulfur dioxide used for the pretreatment is higher than about 20 wt % based on dry weight of lignocellulosic biomass. For example, when the pretreatment temperature is 130° C., we have found that xylose yields are very stable for pretreatment times up to about 3-3.5 hours. Even at the longest pretreatment times tested (e.g., 360 hours, where xylose degradation was evident), xylose recovery was greater than 80% for wheat straw.

More surprisingly, it has been found that the low temperature $SO_2$ pretreatment (e.g., between 110° C. and 150° C.) can result in high glucose yield even when the pretreated material visually bears a resemblance to the lignocellulosic biomass before it is pretreated with the sulfur dioxide and/or sulfurous acid. For example, it has been found that the low temperature $SO_2$ pretreatment of wheat straw can produce a high glucose yield even when the pretreated material looks like a slightly darker version of the wheat straw prior to $SO_2$ pretreatment. Conventional acid pretreatment generally causes a significant visual change in the lignocellulosic biomass. For example, conventional acid pretreatment of wheat straw typically produces a colour change from yellowish brown to dark brown, where the colour of both insoluble and soluble fractions of the pretreated biomass darkens as the severity of the pretreatment increases. In addition, the texture of the biomass can change. For example, when subject to $H_2SO_4$-catalyzed steam pretreatment at 185° C., fibrous native wheat straw can soften and/or degrade to the point that the pretreated material resembles a fine dark brown mud. Although this "muddy" texture makes the pretreated material more difficult to pump, filter, mix with enzymes, etc., it is generally associated with a breakdown in the cell wall structure that allows for greater accessibility to cellulase enzymes. For example, steam explosion, which disrupts the plant cell wall architecture and can even reduce particle size, has been often regarded as one of the most efficient pretreatments. The fact that low temperature $SO_2$ pretreatment can produce a high glucose yield even when the pretreated material substantially maintains the shape and/or size of the untreated material, may improve the process. For example, it may make the pretreated material easier to pump, wash, filter, and/or mix with enzymes (e.g., particularly when the lignocellulosic material is fibrous).

Advantageously, it has been found that the low temperature $SO_2$ pretreatment can provide a high glucose yield even when conducted as a simple "acid pretreatment." More specifically, it has been found that by sufficiently increasing the pretreatment time and/or total amount of $SO_2$, a high glucose yield can be achieved without having to add the amount of alkali required for sulfite pretreatment (e.g., Sulfite Pretreatment to Overcome Recalcitrance of Lignocellulose, or SPORL), the amount of organic solvent associated with organosolv type processes (e.g., $SO_2$-ethanol-water (SEW) pulping), and/or the carbonyl compounds (e.g., acetaldehyde) associated with α-hydroxysulfonic acid pretreatment.

The use of large amounts of added components (e.g., alkali, organic solvent, or carbonyl compounds) tends to make the corresponding processes excessively complex and/or costly. For example, adding alkali for a sulfite type process can necessitate dealing with sulfite waste liquors. In addition, while the addition of alkali may facilitate lignin removal, it can also increase the pH of the process to the point that xylose and/or glucose yield is negatively affected. For example, sulfite pulping, which uses salts of sulfurous acid, is typically carried out between pH 1.5 and 5, depending on the counter ion to sulfite/bisulfite (e.g., $Na^+$, $Ca^+$, $K^+$, $Mg^+$, or $NH_4^+$) and the ratio of base to sulfurous acid. In contrast, solutions of sulfur dioxide and/or sulfurous acid can reach lower pH values (e.g., below 1.5, below 1.25, or below 1). Providing an initial pH below 1.5, and particularly below 1.25, is believed to facilitate hemicellulose solubilization. In addition, low temperature $SO_2$ pretreatment can produce lignosulfonic acids. Since lignosulfonic acid can have a pH below 1.5, and often below 1, it can be used to further reduce the pH. In any case, providing a low temperature $SO_2$ pretreatment, wherein the severity is increased with at least one of a relatively high amount of $SO_2$ and a long pretreatment time, can provide a relatively high xylose and glucose yield with minimal or no added alkali, organic solvent, and/or carbonyl compounds.

Figure 2:
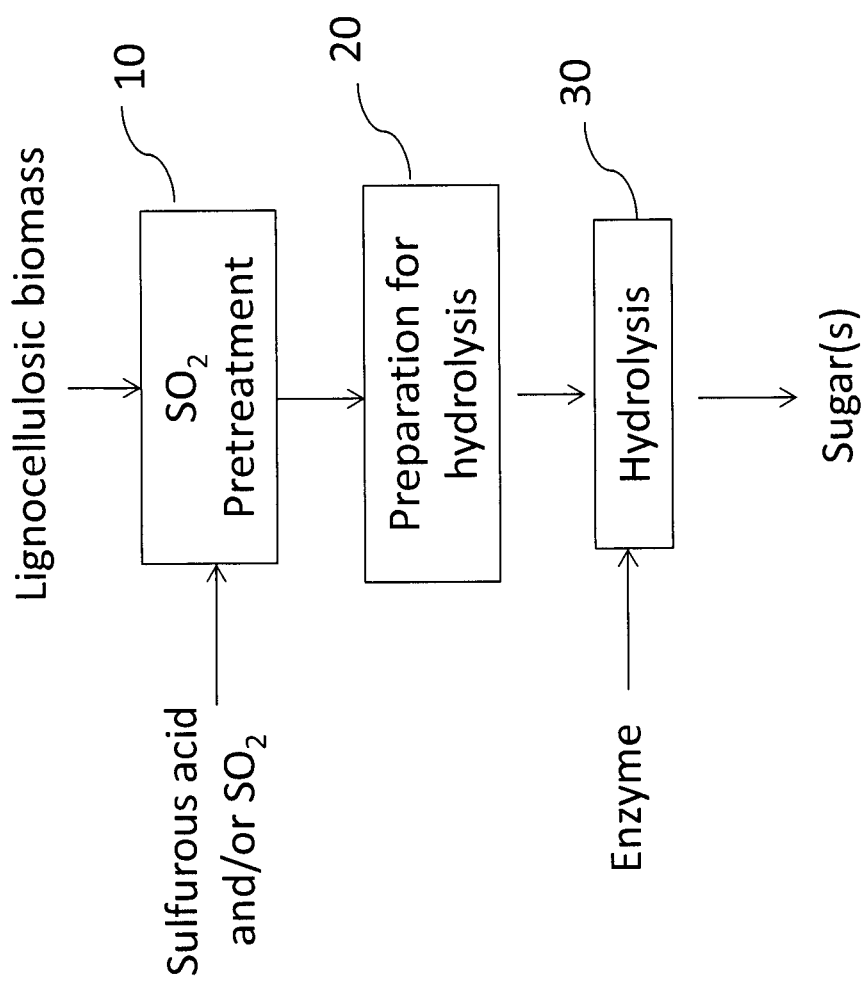
FIG. 2 is a block flow diagram of a method according to one embodiment of the invention.

Referring to FIG. 2, there is shown a method in accordance with one embodiment of the invention. Lignocellulosic biomass is subjected to an $SO_2$ pretreatment 10, which includes heating the lignocellulosic biomass in the presence of sulfur dioxide and/or sulfurous acid at a temperature between about 110° C. and about 150° C. for more than about 90 minutes. During this heating step the $SO_2$ is present in a total amount greater than about 20 wt % (w/w based on dry weight of incoming lignocellulosic biomass). The $SO_2$ pretreated material is then prepared 20 for hydrolysis (e.g., flashed, filtered, washed, cooled, and/or pH adjusted) and at least the solid fraction thereof is hydrolyzed 30 with added enzyme. The hydrolysis 30 produces sugar(s) (e.g., the cellulose in the pretreated material is converted to glucose).

Optionally, the glucose produced during the hydrolysis 30 is fermented (e.g., as part of a separate fermentation step or as part of a simultaneous hydrolysis/fermentation). For example, in one embodiment, the glucose is fermented to an alcohol (e.g., ethanol or butanol), which may be recovered in an optional alcohol recovery step. In one embodiment, the glucose from the hydrolysis 30 is fermented to ethanol using yeast (*Saccharomyces cerevisiae*). In one embodiment, the glucose from hydrolysis 30 is fermented along with C5 sugar derived from pretreatment using a microbe that can ferment both C6 and C5 sugars.

Lignocellulosic Biomass

In general, the lignocellulosic biomass fed to the pretreatment may include and/or be derived from any lignocellulosic feedstock that needs to be pretreated in order to improve enzymatic digestibility. The term "lignocellulosic biomass", as used herein, refers to any type of biomass containing cellulose, hemicellulose, and lignin. For example, in one embodiment, the lignocellulosic biomass has a combined content of cellulose, hemicellulose, and lignin that is greater than 25 wt %. In one embodiment, the lignocellulosic biomass has a combined content of cellulose, hemicellulose, and lignin that is greater than 50 wt %. In one embodiment, the lignocellulosic biomass has a combined content of cellulose, hemicellulose, and lignin that is greater than 75 wt %. In one embodiment, sucrose, fructose, and/or starch are also present, but in lesser amounts than cellulose and hemicellulose.

Some examples of suitable lignocellulosic feedstock include: (i) energy crops; (ii) residues, byproducts, or waste from the processing of plant biomass in a facility or feedstock derived therefrom; (iii) agricultural residues; (iv) forestry biomass; (v) waste material derived from pulp and paper products; (vi) pulp and paper waste; and/or (vii) municipal waste including components removed from municipal waste.

Energy crops include biomass crops such as grasses, including C4 grasses, such as switch grass, energy cane, sorghum, cord grass, rye grass, *miscanthus*, reed canary grass, C3 grasses such as *Arundo donax*, or a combination thereof.

Residues, byproducts, or waste from the processing of plant biomass include residues remaining after obtaining sugar from plant biomass (e.g., sugar cane bagasse, sugar cane tops and leaves, beet pulp, Jerusalem artichoke residue), and residues remaining after grain processing (e.g., corn fiber, corn stover, and bran from grains). Agricultural residues include, but are not limited to soybean stover, corn stover, sorghum stover, rice straw, sugar cane tops and/or leaves, rice hulls, barley straw, wheat straw, canola straw, oat straw, oat hulls, corn fiber, and corn cobs.

Forestry biomass includes hardwood, softwood, recycled wood pulp fiber, sawdust, trimmings, and/or slash from logging operations. Pulp and paper waste includes waste from chemical pulping such as black liquor, spent sulfite liquor, sludge, and/or fines.

Municipal waste includes post-consumer material or waste from a variety of sources such as domestic, commercial, institutional and/or industrial sources. For example, in one embodiment, the lignocellulosic feedstock includes refuse from waste collection and/or sewage sludge.

In one embodiment, the lignocellulosic feedstock is an energy or biomass crop. In one embodiment, the lignocellulosic feedstock comprises an agricultural residue. In one embodiment, the lignocellulosic feedstock comprises a non-woody lignocellulosic feedstock. In one embodiment, the lignocellulosic feedstock comprises hardwood. In one embodiment, the lignocellulosic feedstock comprises wheat straw, or another straw. In one embodiment, the lignocellulosic feedstock comprises stover. As used herein, the term "straw" refers to the stem, stalk and/or foliage portion of crops remaining after the removal of starch and/or sugar containing components for consumption. Examples of straw include, but are not limited to sugar cane tops and/or leaves, bagasse, oat straw, wheat straw, rye straw, rice straw and barley straw. The term "stover" includes the stalk and foliage portion of crops after the removal of starch and/or sugar containing components of plant material for consumption. Examples of stover include, but are not limited to, soybean stover, sorghum stover, and corn stover. In one embodiment, the lignocellulosic feedstock is a mixture of fibers that originate from different kinds of plant materials, including mixtures of cellulosic and non-cellulosic feedstocks. In one embodiment, the lignocellulosic feedstock is a second generation feedstock.

Biomass Preparation

In general, the lignocellulosic biomass may be subjected to one or more optional preparatory steps prior to the pretreatment and/or as part of the pretreatment. Some examples of biomass preparation include size reduction, washing, leaching, sand removal, soaking, wetting, slurry formation, dewatering, plug formation, addition of heat, and addition of chemicals (e.g., pretreatment and/or other). In general, these preparatory steps may depend on the type of biomass and/or the selected pretreatment conditions.

In one embodiment, the lignocellulosic biomass is subjected to a size reduction. Some examples of size reduction methods include milling, grinding, agitation, shredding, compression/expansion, and/or other types of mechanical action. Size reduction by mechanical action may be performed by any type of equipment adapted for the purpose, for example, but not limited to, hammer mills, tub-grinders, roll presses, refiners, hydropulpers, and hydrapulpers. In one embodiment, lignocellulosic feedstock having an average particle size that is greater than about 6-8 inches is subject to a size reduction wherein at least 90% by volume of the particles produced from the size reduction have a length between about 1/16 inch and about 6 inches.

In one embodiment, the lignocellulosic biomass is washed and/or leached with a liquid (e.g., water and/or an aqueous solution). Washing, which may be performed before, during, or after size reduction, may remove sand, grit, fine particles of the lignocellulosic feedstock, and/or other foreign particles that otherwise may cause damage to the downstream equipment. Leaching, which may be performed before, during, or after size reduction, may remove soluble components from the lignocellulosic feedstock. Leaching may remove salts and/or buffering agents.

In one embodiment, the lignocellulosic biomass is subject to sand removal. For example, in one embodiment, the lignocellulosic biomass is washed to remove sand. Alternatively, or additionally, sand may be removed using other wet or dry sand removal techniques that are known in the art (e.g., including the use of a hydrocyclone or a sieve).

In one embodiment, the lignocellulosic biomass is slurried in liquid (e.g., water), which allows the lignocellulosic biomass to be pumped. In one embodiment, the lignocellulosic biomass is slurried subsequent to size reduction, washing, and/or leaching. The desired weight ratio of water to dry biomass solids in the slurry may be determined by factors such as pumpability, pipe-line requirements, and other practical considerations. In general, slurries having a consistency less than about 10 wt % may be pumped using a relatively inexpensive slurry pump.

In one embodiment, the lignocellulosic biomass is soaked in water and/or an aqueous solution (e.g., comprising a pretreatment chemical). Soaking the lignocellulosic biomass may allow pretreatment chemical(s) to more uniformly impregnate the biomass, which in turn may provide even cooking in the heating step of pretreatment. For example, soaking the feedstock in a solution comprising a pretreatment chemical (e.g., such as sulfuric acid and/or sulfurous acid) typically provides uniform impregnation of the biomass with the pretreatment chemical. Soaking the feedstock in water, may allow gaseous pretreatment chemicals (e.g., sulfur dioxide) to more uniformly and/or completely impregnate the lignocellulosic biomass during subsequent chemical addition steps. In general, soaking may be carried out at any suitable temperature and/or for any suitable duration.

In one embodiment, the lignocellulosic biomass is wet with a liquid (e.g., water or an aqueous solution) or steam in order to moisten the lignocellulosic biomass and provide a desired consistency. In general, the term consistency refers the amount of undissolved dry solids or "UDS" in a sample, and is often expressed as a ratio on a weight basis (wt:wt), or as a percent on a weight basis, for example, % (w/w), also denoted herein as wt %. For example, consistency may be determined by filtering and washing the sample to remove dissolved solids and then drying the sample at a temperature and for a period of time that is sufficient to remove water from the sample, but does not result in thermal degradation of the sample. The dry solids are weighed. The weight of water in the sample is the difference between the weight of the sample and the weight of the dry solids. Providing lignocellulosic biomass with a higher consistency to pretreatment may advantageously reduce heating requirements (e.g., since there is less liquid to heat).

In one embodiment, the lignocellulosic biomass is at least partially dewatered (e.g., to provide a specific consistency). In one embodiment, the lignocellulosic biomass is at least partially dewatered in order to increase the undissolved solids content relative to the incoming biomass. In one embodiment, the lignocellulosic biomass is at least partially dewatered in order to remove at least some of the liquid introduced during washing, leaching, slurrying, and/or soaking. In one embodiment, dewatering is achieved using a drainer, filtration device, screen, screw press, and/or extruder. In one embodiment, dewatering is achieved using a centrifuge. In one embodiment, the dewatering is achieved prior to and/or as part of plug formation. In general, plug formation may be considered an integration of lignocellulosic biomass particles into a compacted mass referred to herein as a plug. Plug formation devices may or may not form a plug that acts as a seal between areas of different pressure. Some examples of plug formation devices that dewater biomass include a plug screw feeder, a pressurized screw press, a co-axial piston screw feeder, and a modular screw device.

As mentioned above, each of the washing, leaching, slurrying, soaking, dewatering, and preheating stages are optional and may or may not be included in the process. In general, if the process is a continuous-flow process, it may be advantageous to include steps of slurrying and dewatering prior to pretreatment in order to improve process economics and efficiency. In addition, providing soaking, preheating, and chemical addition steps upstream of the acid pretreatment may provide a more uniform and/or efficient acid pretreatment.

Pretreatment

In general, the pretreatment includes subjecting the lignocellulosic biomass to a pretreatment with sulfur dioxide. Sulfur dioxide ($SO_2$) is a gas, which when dissolved in water, may be referred to as sulfurous acid ($H_2SO_3$). The term "pretreating" or "pretreatment", as used herein, refers to one or more steps where the lignocellulosic biomass is treated to improve the enzymatic digestibility thereof (e.g., where the structure of the lignocellulosic biomass is disrupted such that the cellulose in the lignocellulosic biomass is more susceptible and/or accessible to enzymes in a subsequent hydrolysis). The term "$SO_2$ pretreatment", as used herein, refers to an acid pretreatment wherein the lignocellulosic biomass is in contact with sulfur dioxide and/or sulfurous acid, and wherein to the extent any alkali is added for the pretreatment it is added in an amount that is less than 0.5 wt % (based on dry weight of incoming lignocellulosic biomass), to the extent any organic solvent is added for the pretreatment it is added in an amount that is less than 5 wt % (based on dry weight of incoming lignocellulosic biomass), and to the extent any carbonyl compound (or precursor) is added to form α-hydroxysulfonic acid for the pretreatment it is added in an amount less than 0.5 wt % (based on dry weight of incoming lignocellulosic biomass).

In one embodiment, the $SO_2$ pretreatment is conducted at a relatively low temperature. More specifically, in one embodiment, the $SO_2$ pretreatment includes heating the lignocellulosic biomass with sulfur dioxide and/or sulfurous acid at one or more temperatures between about 110° C. and about 150° C. Using pretreatment temperatures between about 110° C. and about 150° C. advantageously avoids the equipment and/or xylose degradation associated with pretreatments at relatively high temperatures (e.g., greater than 160° C.).

In one embodiment, the pretreatment time and/or total amount of $SO_2$ is selected to convert most of the hemicellulose component to soluble sugars (e.g., xylose, mannose, arabinose, and glucose), but little of the cellulose component to sugars (e.g., which may be hydrolyzed in a subsequent enzymatic hydrolysis). For example, in one embodiment, the degree of pretreatment is selected such that the amount of xylan hydrolyzed to xylose is greater than about 50 wt %, about 60 wt %, about 70 wt %, about 80 wt %, or about 90 wt %.

In one embodiment, the pretreatment time and/or total amount of $SO_2$ provided is selected to provide a pretreatment severity that improves enzyme digestibility of the lignocellulosic biomass. For example, it has been found that when the pretreatment temperature is 130° C., and the total amount of sulfur dioxide is between 20 wt % and 45 wt % based on dry weight of lignocellulosic biomass, that enzymatic digestibility of wheat straw is substantially improved when the pretreatment time is greater than 120 minutes, and significantly improved when the pretreatment time is greater than 180 minutes. When the total amount of sulfur dioxide is about 74 wt % based on dry weight of lignocellulosic biomass, the enzymatic digestibility of wheat straw has been found to be good when the pretreatment time is 180 minutes. In general, providing a pretreatment time that is at least 90 minutes and a total amount of sulfur dioxide that is at least about 25 wt % based on dry weight of lignocellulosic biomass has been shown to provide good hydrolysis for both wheat straw and bagasse that are washed with water after pretreatment.

The term "total amount of sulfur dioxide", as used herein, refers to the total amount of sulfur dioxide and/or sulfurous acid provided for the pretreatment per amount of lignocellulosic biomass on a dry weight basis. In general, the "total amount of sulfur dioxide" is calculated from the grams of sulfur dioxide present initially per gram of dry weight of lignocellulosic biomass present (e.g., as a weight percentage (wt %)). For example, if 25 g of gaseous sulfur dioxide is added to 100 g of lignocellulosic biomass having total solids (TS) content of 93.25% (e.g., 6.75% moisture content), the total amount of sulfur dioxide is calculated as follows:

$$\text{Total amount of SO2} = \frac{\text{g SO2 added}}{\text{g biomass added} * TS \text{ content}} = \frac{25 \text{ g SO2}}{(100 \text{ g biomass}) * 0.9325} = 27 \text{ wt \%}$$

Alternatively, if 52 mL of sulfurous acid prepared to be about 6% (w/w) $H_2SO_3$ is added to 6.43 g of lignocellulosic biomass having a total solids (TS) content of 93.25% (e.g., 6.75% moisture content), the total amount of sulfur dioxide is calculated as:

$$\text{Total amount of SO2} = \frac{\text{g SO2 added}}{\text{g biomass added} * TS \text{ content}} =$$

$$\frac{\text{volume H2SO3(mL)added} * \text{density of H2SO3}\left(\frac{g}{mL}\right) * \frac{6 \text{ g}}{100 \text{ g}} * \frac{Mw \text{ SO2}}{Mw \text{ H2SO3}}}{\text{g biomass added} * TS \text{ content}} =$$

$$\frac{52 * 1.03 * 6 * 64.066/(100 * 82.07)}{6.43 * 0.9325} = 42 \text{ wt \%}$$

In some cases, the total amount of sulfur dioxide can be represented by the $SO_2$ loading. The term "$SO_2$ loading" is often used for continuous systems, where it refers to the amount of $SO_2$ fed to the pretreatment system per amount of dry lignocellulosic biomass fed to the pretreatment system (e.g., calculated from the grams of $SO_2$ provided per gram of dry weight lignocellulosic biomass (e.g., as a weight percentage (wt %)). However, in some cases, the total amount of $SO_2$ can be higher than the $SO_2$ loading (e.g., if some $SO_2$ is held within the pretreatment system when the pretreated lignocellulosic biomass is discharged). For example, in PCT Application No. PCT/CA2016/051089, filed on Sep. 16, 2016, a pretreatment system having a charge of $SO_2$ is disclosed. In this case, the total amount of sulfur dioxide provided includes the amount of $SO_2$ provided in the charge of $SO_2$.

In one embodiment, the $SO_2$ pretreatment includes contacting the lignocellulosic biomass with sulfur dioxide and/or sulfurous acid at one or more temperatures between about 110° C. and about 150° C., for more than about 90 minutes, where the total amount of $SO_2$ is greater than 35 wt % (i.e., w/w based on dry weight of lignocellulosic biomass).

In one embodiment, the $SO_2$ pretreatment includes contacting the lignocellulosic biomass with sulfur dioxide and/or sulfurous acid at one or more temperatures between about 110° C. and about 150° C., for more than about 90 minutes, where the total amount of sulfur dioxide is greater than 50 wt % (i.e., w/w based on dry weight lignocellulosic biomass).

In one embodiment, the $SO_2$ pretreatment includes contacting the lignocellulosic biomass with sulfur dioxide and/or sulfurous acid at one or more temperatures between about 110° C. and about 150° C., for more than about 60 minutes, where the total amount of $SO_2$ is greater than 70 wt % (i.e., w/w based on dry weight lignocellulosic biomass).

In one embodiment, the $SO_2$ pretreatment includes contacting the lignocellulosic biomass with sulfur dioxide and/or sulfurous acid at one or more temperatures between about 110° C. and about 150° C., for more than about 100 minutes, where the total amount of $SO_2$ is greater than 30 wt % (i.e., w/w based on dry weight lignocellulosic biomass).

In one embodiment, the $SO_2$ pretreatment includes contacting the lignocellulosic biomass with sulfur dioxide and/or sulfurous acid at one or more temperatures between about 110° C. and about 150° C., for more than about 120 minutes, where the total amount of $SO_2$ is greater than 25 wt % (i.e., w/w based on dry weight lignocellulosic biomass).

In one embodiment, the $SO_2$ pretreatment includes contacting the lignocellulosic biomass with sulfur dioxide and/or sulfurous acid at one or more temperatures between about 110° C. and about 150° C., for more than about 180 minutes, where the total amount of sulfur dioxide is greater than 20 wt % and less than 100 wt %, based on dry weight lignocellulosic biomass.

Surprisingly, it has been found that the glucose yield achieved with a $SO_2$ pretreatment conducted between about 110° C. and about 150° C. can be similar to a high temperature $SO_2$ pretreatment (e.g., at 230° C., 21 wt % $SO_2$, 3.7 minutes, 10 wt % consistency) and/or better than a high temperature $H_2SO_4$-catalyzed steam pretreatment (e.g., at 200° C., 1.26 wt % $H_2SO_4$, 2 minutes, 30 wt % consistency).

Without being bound by theory, this high glucose yield is attributed to the fact that the low temperature $SO_2$ pretreatment, which is an acid pretreatment, targets dissolution of both hemicellulose and lignin when a relatively high amount of total sulfur dioxide and/or long pretreatment time is used.

The relative importance of hemicellulose dissolution versus lignin dissolution is debatable. While acid pretreatments typically target hydrolysis of hemicelluloses, they are often associated with lignin condensation. In contrast, sulfite pretreatments typically rely on delignification to improve enzymatic hydrolysis. However, since increased lignin removal is associated with relatively high pH values (e.g., at which xylose yield can be compromised), sulfite pretreatment may not be ideal for xylose recovery, and may not sufficiently improve enzymatic digestibility. In U.S. Pat. No. 9,243,364, Zhu et al. disclose a two stage process including a first stage, where the lignocellulosic biomass is subjected to a bisulfite cook where the pH>3 (e.g., a neutral bisulfite cook) to promote delignification and lignin sulfonation, and a second stage, where the pH of the solution is decreased (e.g., to a pH between 1 and 3 by adding $H_2SO_4$) in order to promote the depolymerization and dissolution of hemicelluloses. In each of the first and second stages the pretreatment temperature is between 150° C. and 200° C., while the total pretreatment time in each stage is less than 90 minutes. In other words, this acid sulfite process, when used for pretreating lignocellulosic biomass, still relies on relatively high temperatures.

The instant inventors have found that by increasing the total amount of $SO_2$ in $SO_2$ pretreatment (e.g., greater than 20 wt % based on dry weight of lignocellulosic biomass) and/or by increasing the pretreatment time (e.g., greater than 90 minutes) the amount of lignin solubilized can exceed 50% without having to add the amount of alkali associated with sulfite pulping based pretreatment and/or without having to add significant amounts of organic solvent to facilitate lignin removal. In addition, the inventors have found that by increasing the total amount of $SO_2$ in $SO_2$ pretreatment (e.g., greater than 20 wt % based on dry weight of lignocellulosic biomass) and/or by increasing the pretreatment time (e.g., greater than 90 minutes) the amount of xylose produced can reach over 80%.

More surprisingly, the inventors have found that by increasing the total amount of $SO_2$ in $SO_2$ pretreatment (e.g., greater than 20 wt % based on dry weight of lignocellulosic biomass) and/or by increasing the pretreatment time (e.g., greater than 90 minutes), the glucose yield at 72 hours of enzymatic hydrolysis can be higher than 80%, while the glucose yield at 96 hours of enzymatic hydrolysis can be higher than 90%, with only 5 mg/g (5 milligrams protein per gram cellulose) of enzyme (i.e., for wheat straw). This is surprising because low temperature $H_2SO_4$ pretreatment does not provide the same increase in enzymatic digestibility, and because it has been previously believed that it was important to bond $SO_2$ to significant amounts of other compounds (e.g., carbonyl compounds) in order to facilitate low temperature pretreatments (α-hydroxysulfonic acid pretreatment).

As discussed above, the low temperature $SO_2$ pretreatment disclosed herein can provide good lignin solubilization, good hemicellulose hydrolysis, and good glucose yield without having to add the amount of alkali associated with sulfite pulping based pretreatments and/or without having to add an amount of organic solvent associated with an organosolv process (e.g., to facilitate lignin removal).

For example, in sulfite pulping based pretreatments the cooking liquor can be prepared by adding counter ions (e.g., sodium, potassium, calcium, or magnesium) to sulfurous acid, often as hydroxide. For example, counter ions can be provided by adding NaOH, KOH, $Ca(OH)_2$, $Mg(OH)_2$, MgO, or CaO. The amount of alkali added (e.g., NaOH or CaO) can be expressed as the weight of alkali per dry weight of lignocellulosic solids. For example, if 0.4 g of NaOH is added to 100 g of lignocellulosic biomass having total solids (TS) content of 93.25% (e.g., 6.75% moisture content), the amount of alkali added is calculated as:

$$\text{Amount of alkali added} = \frac{\text{g alkali added}}{\text{g biomass added} * TS \text{ content}} = \frac{0.4\ g}{(100\ \text{g biomass}*)*0.9325} = 0.43\ wt\ \%$$

In general, the amount of alkali chemical added in sulfite pulping based pretreatments is greater than about 1 wt % based on dry weight of lignocellulosic biomass. For example, US Pat. Appl. Pub. No. 20110250638 indicates that the amount of base (hydroxide ion) is from 1 to 10% w/w, preferably, from 2% to 7%. Advantageously, the low temperature $SO_2$ pretreatment disclosed herein can improve hydrolysis without the addition of alkali chemical. However, in some embodiments, alkali and/or solvent may be introduced into the low temperature $SO_2$ pretreatment. In general, the amount of alkali added will be less than about 0.5 wt % based on dry weight of lignocellulosic biomass and/or the amount of solvent added will be less than about 5 wt % based on dry weight of lignocellulosic biomass. In one embodiment the amount of alkali added for pretreatment is less than 0.4 wt % based on dry weight of lignocellulosic biomass. In one embodiment the amount of alkali added for pretreatment is less than 0.25 wt % based on dry weight of lignocellulosic biomass. In one embodiment the amount of alkali added for pretreatment corresponds to a bisulfite loading that is less than 1 wt % based on dry weight of lignocellulosic biomass. In one embodiment the amount of alkali added for pretreatment corresponds to a bisulfite loading that is less than 0.5 wt % based on dry weight of lignocellulosic biomass. In one embodiment, the amount of bisulfite salt formed for pretreatment is less than 2 wt % based on dry weight lignocellulosic biomass. In one embodiment, the amount of bisulfite salt formed for pretreatment is less than 1 wt % based on dry weight lignocellulosic biomass.

In some cases, mildly alkaline compounds are introduced into the pretreatment via a recycle or backset stream. For example, in one embodiment, compounds derived from the native lignocellulosic feedstock are introduced into pretreatment via a recycle stream (e.g., leach water may be high in potassium bicarbonate). When calculating the amount of alkali added with these compounds for pretreatment (e.g., less than 0.5 wt % based on dry weight of lignocellulosic biomass), the amount of equivalent OH alkali chemical provided for pretreatment is used.

In one embodiment, alkali is added for the pretreatment in an amount in the range from 0 to 0.5 wt % based on dry weight of incoming lignocellulosic biomass. In one embodiment, organic solvent is added for the pretreatment in an amount in the range from 0 to 5 wt % based on dry weight of incoming lignocellulosic biomass. In one embodiment, carbonyl compound (e.g., aldehyde), or precursor, for forming α-hydroxysulfonic acid is added for the pretreatment in an amount in the range from 0 to 0.5 wt % based on dry weight of incoming lignocellulosic biomass.

In cases where the native lignocellulosic biomass has a high alkali content and/or small amounts of alkali are added, it may be advantageous to characterize the pH of the system. For example, the amount of sulfur dioxide and/or sulfurous acid provided can be represented using initial pH. Initial pH is measured at ambient temperature after all of the sulfur dioxide and/or sulfurous acid has been added to the lignocellulosic biomass and before heating begins. In one embodiment, sufficient sulfur dioxide and/or sulfurous acid is added to provide an initial pH less than 1.5 measured at ambient temperature. In one embodiment, sufficient sulfur dioxide and/or sulfurous acid is added to provide an initial pH less than 1.25, measured at ambient temperature. In one embodiment, sufficient sulfur dioxide and/or sulfurous acid is added to provide an initial pH less than 1, measured at ambient temperature. In embodiments where it is difficult to measure initial pH, the amount of sulfur dioxide and/or sulfurous acid added can be reflected using final pH. Final pH is measured at ambient temperature after the pretreated material is discharged from the pretreatment reactor(s). In embodiments wherein the pretreated biomass has a large undissolved solids content and/or is relatively thick, the final pH is measured from a filtrate, pressate, or centrate of the sample (e.g., or other liquid from a solids-liquid separation). In practice, the final pH can be lower than the initial pH. In one embodiment, sufficient sulfur dioxide and/or sulfurous acid is added to provide a final pH less than 1.25, measured at ambient temperature. In one embodiment, sufficient sulfur dioxide and/or sulfurous acid is added to provide a final pH less than 1, measured at ambient temperature. In one embodiment, sufficient sulfur dioxide and/or sulfurous acid is added to provide a final pH less than 0.8, measured at ambient temperature. Evaluating the amount of sulfur dioxide and/or sulfurous acid used in the $SO_2$ pretreatment with pH is advantageous in that the severity of pretreatment processes are often calculated based on the pH.

In one embodiment, the $SO_2$ pretreatment is conducted on lignocellulosic biomass having a solids consistency between about 5 wt % and about 51 wt %. As used herein, the terms "consistency" and "solids consistency" are interchangeable and refer to the weight of insoluble solids per weight of slurry, expressed as a percentage. In one embodiment, the $SO_2$ pretreatment is conducted on lignocellulosic biomass having a consistency between about 8 wt % and about 35 wt %. In one embodiment, the $SO_2$ pretreatment is conducted on lignocellulosic biomass having a consistency between about 12 wt % and about 25 wt %. In embodiments where the pretreatment involves adding gaseous sulfur dioxide to the lignocellulosic biomass, using a consistency that is between about 10 wt % and 35 wt % advantageously provides a reasonable compromise between providing sufficient moisture for a successful pretreatment with $SO_2$, without overwhelming the system with excess water.

The $SO_2$ pretreatment may be carried out in batch mode, semi-batch mode, or continuous mode, in one or more pretreatment reactors. For example, the pretreatment may be conducted in one or more vertical reactors, horizontal reactors, inclined reactors, or any combination thereof.

In one embodiment, the $SO_2$ pretreatment is carried out in batch mode in a steam autoclave. In one embodiment, the $SO_2$ pretreatment is conducted in a plug flow reactor. In one embodiment, the $SO_2$ pretreatment is conducted in a counter-current flow reactor. In one embodiment the $SO_2$ pretreatment is conducted in reactor provided with a charge of sulfur dioxide as described in as illustrated in PCT Application No. PCT/CA2016/051089, filed on Sep. 16, 2016.

In one embodiment, the $SO_2$ pretreatment is conducted in a pretreatment system, which may include a plurality of components/devices in addition to a pretreatment rector. Some examples of these devices/components include a biomass conveyer, washing system, dewatering system, a plug formation device, a heating chamber, a high shear heating chamber, a pre-steaming chamber, an $SO_2$ impregnation chamber, vapour reservoir chamber, an additional pretreatment reactor, connecting conduits, valves, pumps, etc.

In one embodiment, the $SO_2$ pretreatment is conducted in a pretreatment system and/or reactor that is pressurizable. For example, in one embodiment, the pretreatment reactor and/or pretreatment system includes a plurality of valves and/or other pressure increasing, pressure decreasing, or pressure maintaining components for providing and/or maintaining the pretreatment reactor at a specific pressure.

In general, the $SO_2$ pretreatment is conducted in a pretreatment system and/or pretreatment reactor that includes a heater, or some other heating means, for heating the lignocellulosic biomass to the pretreatment temperature. For example, in one embodiment, the pretreatment reactor is clad in a heating jacket. In another embodiment, the pretreatment reactor and/or the pretreatment system includes direct steam injection inlets. In one embodiment, the lignocellulosic biomass is heated (e.g., directly or indirectly) in the pretreatment reactor. In one embodiment, the lignocellulosic biomass is heated both upstream of and in the pretreatment reactor. In any case, direct steam injection may be advantageous in terms of quickly and uniformly heating high consistency biomass and/or for breaking down the biomass structure via steam explosion (e.g., if used).

In general, the $SO_2$ pretreatment includes adding sulfur dioxide and/or sulfurous acid to the lignocellulosic material, which may be in the form of freshly-added $SO_2$, make-up $SO_2$, and/or recycled $SO_2$ (e.g., recycled from previous pretreatment reactions). The $SO_2$ may be added to the lignocellulosic biomass before entering the pretreatment reactor, within the pretreatment reactor, or a combination thereof. For example, the $SO_2$ may be added to the lignocellulosic biomass via separate inlets or via the same inlet. For example, in one embodiment, the lignocellulosic biomass is soaked in an aqueous sulfurous acid solution prior to entering the pretreatment reactor. In one embodiment, an aqueous slurry of lignocellulosic biomass is fed to the pretreatment reactor and gaseous sulfur dioxide is injected therein (e.g., bubbled into the slurry). In one embodiment, a slurry of lignocellulosic biomass and sulfurous acid is fed into the pretreatment reactor, and the pressure is increased by adding gaseous sulfur dioxide.

At the end of the $SO_2$ pretreatment, the pretreated lignocellulosic biomass may be discharged from the pretreatment reactor and/or system. In one embodiment, this includes reducing the pressure on the pretreated lignocellulosic biomass. In general, the pressure may be released slowly or quickly. Alternatively, the pressure may be reduced at a stage further downstream. In one embodiment, the pressure is reduced by flashing.

Preparing the Pretreated Biomass for Enzymatic Hydrolysis

In general, the $SO_2$ pretreated material is subject to one or more steps to prepare it for hydrolysis, if required. For example, in one embodiment the $SO_2$ pretreated material is subject to a pressure reduction (e.g., flashing), a liquid/solid separation (e.g., filtering), a washing step, a cooling step, and/or a pH adjustment step.

In one embodiment, the $SO_2$ pretreated biomass is subject to a pressure reduction. For example, in one embodiment, the pressure is reduced using one or more flash tanks in fluid connection with the pretreatment reactor. Flashing may reduce the temperature of the $SO_2$ pretreated biomass to 100° C. if an atmospheric flash tank, or lower if a vacuum flash tank.

In one embodiment, the $SO_2$ pretreated biomass is subject to a liquid/solid separation, which provides a solid fraction and a liquid fraction. The solid fraction may contain undissolved solids such as unconverted cellulose and/or insoluble lignin. The liquid fraction, which may also be referred to as the xylose-rich fraction, may contain soluble compounds such as sugars (e.g., xylose, glucose, and arabinose), organic acids (e.g., acetic acid and glucuronic acid), soluble lignin (e.g., including soluble products of reactions between sulfur dioxide/sulfurous acid and lignin, such as lignosulfonic acids), soluble sugar degradation products (e.g., furfural, which may be derived from C5 sugars, and hydroxymethylfurfural (HMF), which may be derived from C6 sugars) and/or one or more salts (e.g., sulfite salts). For example, in one embodiment, the $SO_2$ pretreated biomass is flashed and then fed to one or more centrifuges that provide a solid stream and a liquid stream.

In one embodiment, the $SO_2$ pretreated biomass is subject to one or more washing steps. For example, in one embodiment, the solid fraction from a solid/liquid separation is washed to remove soluble components, including potential inhibitors and/or inactivators. Washing may also remove lignin (e.g., sulfonated lignin). In one embodiment, the $SO_2$ pretreated biomass is washed as part of the liquid/solid separation (e.g., as part of decanter/wash cycle). The $SO_2$ pretreated biomass may be washed as part of the liquid/solid separation at high or low pressure, which may or may not reduce the temperature of the pretreated biomass. In one embodiment, the wash water is reused or recycled. In one embodiment, the wash water and the liquid fraction are fed to fermentation. In one embodiment, lignin and/or lignosulfonic acid is extracted from the wash water.

In one embodiment, the $SO_2$ pretreated biomass is subjected to one or more cooling steps. For example, in one embodiment, the $SO_2$ pretreated biomass is cooled to within a temperature range compatible with enzyme(s) added for the enzymatic hydrolysis. For example, conventional cellulases often have an optimum temperature range between about 40° C. and about 60° C., and more commonly between about 50° C. and 55° C., whereas thermostable and/or thermophilic enzymes may have optimum temperatures that are much higher (e.g., as high as, or greater than 80° C.). In one embodiment, the $SO_2$ pretreated biomass is cooled to within a temperature range compatible with enzyme(s) and yeast used in a simultaneous saccharification and fermentation (SSF).

In one embodiment, cooling is provided primarily from flashing. In one embodiment, cooling is provided primarily using a heat exchanger. In one embodiment, cooling is provided primarily by washing the solids. In one embodiment, cooling is provided by any combination of flashing, heat exchange, washing, and other cooling techniques. In one embodiment, cooling is provided by injecting a fluid into the pretreated biomass. For example, in one embodiment, cooling is achieved when alkali and/or water is added to the pretreated biomass into order to provide the pH and/or consistency desired for enzymatic hydrolysis.

Advantageously, since the $SO_2$ pretreatment is conducted at relatively low temperatures (e.g., between 110° C. and 150° C.), the one or more cooling steps may not have to produce a significant temperature drop.

In one embodiment, the $SO_2$ pretreated biomass is subjected to one or more pH adjustment steps. In one embodiment, the pH of the $SO_2$ pretreated biomass is adjusted to within a range near the pH optimum of the enzyme(s) used in hydrolysis. For example, cellulases typically have an optimum pH range between about 4 and about 7, more commonly between about 4.5 and about 5.5, and often about 5. In one embodiment, the pH is adjusted to between about 4 and about 8. In one embodiment, the pH is adjusted to between about 4.5 and about 6. In one embodiment, the pH is adjusted so as to substantially neutralize the pretreated biomass.

In one embodiment, the pH of the $SO_2$ pretreated biomass is increased as a result of the washing step. In one embodiment, the pH of the $SO_2$ pretreated biomass is increased by adding alkali (e.g., calcium hydroxide, potassium hydroxide, sodium hydroxide, ammonia gas, etc.). For example, in one embodiment, sufficient alkali is added to increase the pH of the pretreated biomass to a pH near the optimum pH range of the enzyme(s) used in hydrolysis. In one embodiment, the pH adjustment step includes adding sufficient alkali to overshoot the optimum pH of the enzyme (e.g., overliming), and then adding acid to reduce the pH to near the optimum pH range of the enzyme(s).

In general, the pH adjustment step may be conducted on the solid fraction, the liquid fraction, and/or a combination thereof, and may be conducted before, after, and/or as part of the one or more cooling steps. For example, in embodiments wherein the pretreated biomass is separated into a solid fraction and a liquid fraction, where only the solid fraction is fed to enzymatic hydrolysis, the pH of the liquid fraction may require adjustment prior to being fed to fermentation (e.g., separate from, or with, the hydrolyzate from the solid fraction). For example, in one embodiment, the pH of the liquid fraction is adjusted to the pH optimum of the microorganism used in a subsequent fermentation step. For example, *Saccharomyces cerevisiae* may have optimum pH values between about 4 and about 5.5.

Advantageously, since the $SO_2$ pretreatment uses a relatively high amount of free $SO_2$ that is not associated with an added compound (e.g., alkali or carbonyl), flashing of the pretreated biomass may remove a large portion of the $SO_2$, and thus increase the pH of the mixture, so that the pH adjustment step(s) may not have to significantly increase the pH and/or may require less alkali.

In one embodiment, enzyme is added to and/or mixed with the pretreated biomass (e.g., either the solid fraction or whole) prior to feeding the pretreated biomass to the hydrolysis reactor. In one embodiment, enzyme addition is after cooling and alkali addition.

As discussed above, the pretreated biomass may be washed. However, it can also be fed to enzymatic hydrolysis with minimal washing, or without washing. While washing may remove potential inhibitors and/or inactivators, and thus increase enzyme efficiency, it may also remove fermentable sugars, and thus reduce ethanol yield. Providing little or no washing of the pretreated biomass is advantageous in that it requires less process water and provides a simpler process. In various laboratory experiments, we have found that following $SO_2$ pretreatment at low temperatures (e.g., between 110° C. and 150° C.), a higher glucose yield can be achieved if the pretreated biomass is washed.

Enzymatic Hydrolysis

The cellulose in the $SO_2$ pretreated biomass can be hydrolyzed to glucose after enzyme addition.

In one embodiment, enzyme addition includes the addition of cellulase, which is an enzyme(s) that breaks cellulose chains into glucose. In particular, the term "cellulase" refers to any of several enzymes produced by fungi, bacteria, or protozoans that catalyze cellulolysis. For example, the term cellulase may denote a multi-enzyme mixture comprising exo-cellobiohydrolases (CBH), endoglucanases (EG), and β-glucosidases (βG) that can be produced by a number of plants and microorganisms. Among the most widely studied, characterized and commercially produced cellulases are those obtained from fungi of the genera *Aspergillus, Humicola, Chrysosporium, Melanocarpus, Myceliopthora, Sporotrichum* and *Trichoderma*, and from the bacteria of the genera *Bacillus* and *Thermobifida*. Cellulase produced by the filamentous fungi *Trichoderma longibrachiatum* comprises at least two cellobiohydrolase enzymes termed CBHI and CBHII and at least four EG enzymes. As well, EGI, EGII, EGIII, EGV and EGVI cellulases have been isolated from *Humicola insolens*. In addition to CBH, EG and βG, there are several accessory enzymes that may aid in the enzymatic digestion of cellulose, including glycoside hydrolase 61 (GH61), swollenin, expansin, lucinen and cellulose-induced protein (Cip). For example, in one embodiment the enzyme added contains GH61, which may improve hydrolysis. In one embodiment, the enzyme added comprises a commercial cellulase composition that is suitable for use in the methods/processes described herein.

In one embodiment, enzyme addition is achieved by adding enzyme to a reservoir, such as a tank, to form an enzyme solution, which is then introduced to the pretreated biomass. In one embodiment, enzyme is added to the washed solid fraction of the pretreated biomass. In one embodiment, enzyme is added to a pH adjusted slurry of pretreated biomass that includes both liquid and solid portions of the pretreated biomass.

In general, the enzyme dose may depend on the activity of the enzyme at the selected pH and temperature, the reaction time, the volume of the reactor, and/or other parameters. It should be appreciated that these parameters may be adjusted as desired by one of skill in the art.

In one embodiment, cellulase is added at a dosage between about 2 to 20 mg protein per gram cellulase. In one embodiment, the cellulase is added at a dosage between about 2 to 15 mg protein per gram cellulase. In one embodiment, the cellulase is added at a dosage between about 2 to 12 mg protein per gram cellulase. The protein may be quantified using either the bicinchoninic acid (BCA) assay or the Bradford assay. In one embodiment, the initial concentration of cellulose in the slurry, prior to the start of enzymatic hydrolysis, is between about 0.01% (w/w) to about 20% (w/w).

In one embodiment, the enzymatic hydrolysis is carried out at a pH and temperature that is at or near the optimum for the added enzyme. For example, in one embodiment, the enzymatic hydrolysis is carried out at one or more temperatures between about 30° C. to about 95° C. In one embodiment, the enzymatic hydrolysis is carried out at one or more temperatures between about 50° C. to about 60° C. In one embodiment, the enzymatic hydrolysis is carried out at one or more temperatures between about 45° C. to about 55° C. In one embodiment, the enzymatic hydrolysis is carried such that the initial pH is, and/or such that the pH is maintained, between about 3.5 and about 8.0. In one embodiment, the enzymatic hydrolysis is carried such that the initial pH is, and/or such that the pH is maintained, between about 4 and about 6. In one embodiment, the enzymatic hydrolysis is carried such that the initial pH is, and/or such that the pH is maintained, between about 4.8 and about 5.5.

In one embodiment, the enzymatic hydrolysis is carried out for a time period of about 10 to about 250 hours. In one embodiment, the enzymatic hydrolysis is carried out for a time period of about 50 to about 250 hours. In one embodiment, the enzymatic hydrolysis is carried out for at least 24 hours. In one embodiment, the enzymatic hydrolysis is carried out for at least 36 hours. In one embodiment, the enzymatic hydrolysis is carried out for at least 48 hours. In one embodiment, the enzymatic hydrolysis is carried out for at least 72 hours. In one embodiment, the enzymatic hydrolysis is carried out for at least 80 hours. In general, conducting the enzymatic hydrolysis for at least 24 hours will promote hydrolysis of both the amorphous and crystalline cellulose.

In general, the enzymatic hydrolysis may be conducted as a batch process, a continuous process, or a combination thereof. In addition, the enzymatic hydrolysis may be agitated, unmixed, or a combination thereof. In one embodiment, the enzymatic hydrolysis is conducted in one or more dedicated hydrolysis reactors, connected in series or parallel. In one embodiment, the one or more hydrolysis reactors are jacketed with steam, hot water, or other heat sources. In one embodiment, oxygen is added to one or more of the hydrolysis reactors.

In one embodiment, the dissolved oxygen concentration within one or more hydrolysis reactors is maintained at a certain level. In one embodiment, the dissolved oxygen concentration is maintained within a range that is sufficient for the full activity of lytic polysaccharide monooxygenases (LMPOs) or any other oxygen-dependent components of the catalyst used to effect hydrolysis. In one embodiment, air or oxygen is bubbled into the slurry or headspace of one or more of the hydrolysis reactors.

In one embodiment, the enzymatic hydrolysis is conducted in one or more continuous stirred tank reactors (CSTRs) and/or one or more plug flow reactors (PFRs). In plug flow reactors, the slurry is pumped through a pipe or tube such that it exhibits a relatively uniform velocity profile across the diameter of the pipe/tube and such that residence time within the reactor provides the desired conversion. In one embodiment, the hydrolysis includes a plurality of hydrolysis rectors including a PFR and a CSTR in series.

In one embodiment, the enzymatic hydrolysis and fermentation are conducted in separate vessels so that each biological reaction can occur at its respective optimal temperature. In one embodiment, the enzymatic hydrolysis and fermentation are conducted is a same vessel, or series of vessels.

In one embodiment, the hydrolyzate provided by enzymatic hydrolysis is filtered to remove insoluble lignin and/or undigested cellulose.

Fermentation

In one embodiment, the sugars produced during enzymatic hydrolysis and/or $SO_2$ pretreatment are fermented via one or more microorganisms. In general, the fermentation microorganism(s) may include any suitable yeast and/or bacteria.

In one embodiment, the hydrolyzate produced during enzymatic hydrolysis is subjected to a fermentation with *Saccharomyces* spp. yeast. For example, in one embodiment, the fermentation is carried out with *Saccharomyces cerevisiae*, which has the ability to utilize a wide range of hexoses such as glucose, fructose, sucrose, galactose, maltose, and maltotriose to produce a high yield of ethanol. In one embodiment, the glucose and/or other hexoses derived from the cellulose are fermented to ethanol using a wild-type *Saccharomyces cerevisiae* or a genetically modified yeast. In one embodiment, the fermentation is carried out with *Zymomonas mobilis* bacteria.

In one embodiment, the hydrolyzate produced during enzymatic hydrolysis is fermented by one or more microorganisms to produce a fermentation broth containing butanol. For example, in one embodiment the glucose produced during enzymatic hydrolysis is fermented to butanol with *Clostridium acetobutylicum*.

In one embodiment, one or more of the pentoses produced during the $SO_2$ pretreatment is fermented to ethanol via one or more organisms. For example, in one embodiment, the xylose and/or arabinose produced during the $SO_2$ pretreatment is fermented to ethanol with a yeast strain that naturally contains, or has been engineered to contain, the ability to ferment these sugars to ethanol. Examples of microbes that have been genetically modified to ferment xylose include recombinant *Saccharomyces* strains into which has been inserted either (a) the xylose reductase (XR) and xylitol dehydrogenase (XDH) genes from *Pichia stipitis*.

In one embodiment, the xylose and other pentose sugars produced during the $SO_2$ pretreatment are fermented to xylitol by yeast strains selected from the group consisting of *Candida, Pichia, Pachysolen, Hansenula, Debaryomyces, Kluyveromyces* and *Saccharomyces*.

In general, the C6 sugar from the enzymatic hydrolysis and the C5 sugars from the liquid fraction of the $SO_2$ pretreated biomass can be subjected to separate fermentations or a combined fermentation. For example, consider the case where the pretreated biomass is subject to a solid/liquid separation and only the solid fraction is fed to enzymatic hydrolysis. In this case, the glucose produced by enzymatic hydrolysis can be fermented on its own, or can be combined with the liquid fraction and then fermented. For example, in one embodiment, a sugar solution containing both the C5 and C6 sugars is fermented to ethanol using only *Saccharomyces cerevisiae*. In one embodiment, a sugar solution containing both C5 and C6 sugars is fermented to ethanol using a mixture wherein C5 utilizing and ethanol producing yeasts (e.g., such as *Pichia fermentans* and *Pichia stipitis*) are cocultured with *Saccharomyces cerevisiae*. In one embodiment, a sugar solution containing both C5 and C6 sugars is fermented using genetically engineered *Saccharomyces* yeast capable of cofermenting glucose and xylose.

In general, the dose of the microorganism(s) will depend on a number of factors, including the activity of the microorganism, the desired reaction time, the volume of the reactor, and/or other parameters. It should be appreciated that these parameters may be adjusted as desired by one of skill in the art to achieve optimal conditions. In one embodiment, the fermentation is supplemented with additional nutrients required for the growth of the fermentation microorganism. For example, yeast extract, specific amino acids, phosphate, nitrogen sources, salts, trace elements and vitamins may be added to the hydrolyzate slurry to support their growth. In one embodiment, yeast recycle is employed.

In one embodiment, the fermentation is carried out at a pH and temperature that is at or near the optimum for the added microorganism. For example, *Saccharomyces cerevisiae* may have optimum pH values between about 4 and about 5.5 and a temperature optimum between about 25° C. and about 35° C. In one embodiment, the fermentation is carried out at one or more temperatures between about 25° C. to about 55° C. In one embodiment, the fermentation is carried out at one or more temperatures between about 30° C. to about 35° C.

In general, the fermentation may be conducted as a batch process, a continuous process, or a fed-batch mode. For example, in one embodiment, the fermentation is conducted in continuous mode, which may offer greater productivity and lower costs. In one embodiment, the enzymatic hydrolysis may be conducted in one or more fermentation tanks, which can be connected in series or parallel. In general, the fermentation may be agitated, unmixed, or a combination thereof. For example, in one embodiment, the fermentation is conducted one or more continuous stirred tank reactors (CSTRs) and/or one or more plug flow reactors (PFRs). In one embodiment, the one or more fermentation tanks are jacketed with steam, hot water, or other heat sources.

In one embodiment, the enzymatic hydrolysis and fermentation are conducted in separate vessels so that each biological reaction can occur at its respective optimal temperature. In another embodiment, the hydrolysis (e.g., which may be also referred to as saccharification) is conducted simultaneously with the fermentation in same vessel. For example, in one embodiment, a simultaneous saccharification and fermentation (SSF) is conducted at temperature between about 35° C. and 38° C., which is a compromise between the 50° C. to 55° C. optimum for cellulase and the 25° C. to 35° C. optimum for yeast.

Alcohol Recovery

Any alcohol produced during fermentation can be recovered, a process wherein the alcohol is concentrated and/or purified from the fermented solution (e.g., which may or may not have been subjected to a solids-liquid separation to remove unconverted cellulose, insoluble lignin, and/or other undissolved substances).

In one embodiment, alcohol recovery uses one or more distillation columns that separate the alcohol from other components (e.g., water). In general, the distillation column(s) in the distillation unit may be operated in continuous or batch mode, although are typically operated in a continuous mode. Heat for the distillation process may be introduced at one or more points, either by direct steam injection or indirectly via heat exchangers. When the alcohol is ethanol, after distillation, the water remaining in the concentrated ethanol stream (i.e., vapour) may be removed from the ethanol rich vapour by a molecular sieve resin, by membrane extraction, or other methods known to those of skill in the art for concentration of ethanol beyond the 95% that is typically achieved by distillation (e.g., a vapour phase drying). The vapour may then be condensed and denatured.

Sulfur Dioxide Recovery

Excess sulfur dioxide not consumed during the pretreatment can be recovered and/or recycled. For example, in one embodiment, the $SO_2$ pretreated biomass is flashed, and the flash stream, which contains excess sulfur dioxide, is fed to a sulfur dioxide recovery unit.

In one embodiment, the sulfur dioxide recovery unit includes a partial condenser that provides a first stream comprising a condensate (e.g., from the steam) and a second stream comprising gaseous sulfur dioxide. Optionally, the condensate is fed to a sulfur dioxide stripper, which removes any residual sulfur dioxide from the condensate. Optionally, the sulfur dioxide gas stream is dried (e.g., by countercurrent washing with 98% sulfuric acid), compressed, and/or condensed.

In one embodiment, the sulfur dioxide recovery unit includes a sulfur dioxide scrubbing system, which may include one or more packed absorbers (e.g., in series), which may be amine-based, alkali-based, or other absorbers. In one embodiment, the sulfur dioxide recovery unit includes a regenerative sulfur dioxide scrubbing system. In one embodiment, the regenerative sulfur dioxide scrubbing system is a wet sulfur dioxide scrubbing system. In one embodiment, the regenerative sulfur dioxide scrubbing system is a dual alkali system using a first alkali absorber to scrub the gas stream, and a second alkali to regenerate the absorber.

In one embodiment, the excess sulfur dioxide is converted into elemental sulfur, which may be used to provide recycled sulfur dioxide. In one embodiment, the sulfur recovery unit comprises a sulfur burner, which burns sulfur in the presence of a high concentration of oxygen, to provide the sulfur dioxide. In one embodiment, the sulfur recovery unit comprises a sulfur burner that uses the flash stream, or a stream derived from the flash stream, to reduce the temperature in the sulfur burner.

In general, gas containing sulfur dioxide having a concentration in the range of about 1% to about 100% may be recovered to provide liquid sulfur dioxide. For example, some processes of purifying and/or condensing sulfur dioxide gas and/or preparing liquid sulfur dioxide, which can be used to provide gas phase sulfur dioxide, include compressing and condensing (e.g., at high sulfur dioxide concentrations), partial condensation (e.g., at low sulfur dioxide concentrations), and absorption and acidification (e.g., scrubbing low concentrations of sulfur dioxide with ammonium bisulfate). For example, at atmospheric pressure pure sulfur dioxide will condense at −10.1° C., and at increased pressures will begin to condense at higher temperatures (i.e., will condense at 32.2° C. at 388 kPa (56.3 psig)).

In one embodiment, the recovered sulfur dioxide, which is optionally stored temporarily, is recycled directly back into the process. In one embodiment, the recycling includes generating gaseous sulfur dioxide from liquid sulfur dioxide for impregnating the lignocellulosic biomass, or forming a sulfurous acid solution that is used to impregnate the lignocellulosic biomass. In one embodiment, gaseous sulfur dioxide is compressed and stored for recycling back into the process.

Advantageously, sulfur dioxide recovery allows the recycling of sulfur within the system, and thus improves the process economics (e.g., since less sulfur dioxide and/or sulfurous acid needs to be purchased for pretreatment). In addition, sulfur dioxide recovery improves the economics of using a high sulfur dioxide loading, particularly, when the sulfur dioxide recovery is efficient at high sulfur dioxide concentrations.

Providing relatively high sulfur dioxide loadings (e.g., either from gaseous sulfur dioxide and/or sulfurous acid) without a volatile solvent (e.g., ethanol) and without added alkali (e.g., NaOH) advantageously facilitates a simple flash steam recovery of sulfur dioxide. In addition, it simplifies any further purification and/or processing of the sulfur dioxide recovered from the flash stream. Since the recovery may be relatively simple and efficient, the cost of the relatively high sulfur loading is not as limiting. Accordingly, the advantages of using a high sulfur loading for low temperature $SO_2$ pretreatment may be exploited.

Advantageously, using a relatively high sulfur loading (e.g., greater than 20 wt %, or greater than 25 wt %, based on dry weight of lignocellulosic biomass) and sulfur dioxide recovery from the flash, when at least 30% to 100% of the $SO_2$ in the flash is recovered and/or recycled improves the economics of the process.

To facilitate a better understanding of embodiments of the instant invention, the following examples of certain aspects of some embodiments are given. In no way should the following examples be read to limit, or define, the entire scope of the invention.

EXAMPLES

Example 1: Low Temperature $SO_2$ Pretreatment of Lignocellulosic Material

Low temperature $SO_2$ pretreatment of wheat straw was conducted in pressure tube reactors (PT), which are 110 mL glass tubes (e.g., about 7 inches in length).

Wheat straw was hammer-milled such that a large portion of the particles was less than about 1 inch (2.54 cm) length and ¼ inch (0.635 cm) width. In general, less than 5% of the particles were longer than 2 inches (5.08 cm) and up to 10% of the particles were fines, the size of dust.

The glucan content of the straw was 34.61%, the xylan content was 20.09%, and the lignin content was 20.49% on a dry basis. The total solids (TS) content of the straw was 93.25%, which equates to 6.75% moisture. The carbohydrate assay was based on Determination of Structural Carbohydrates and Lignin in Biomass-LAP (Technical Report NREL/TP-510-42618).

Solutions of 6%, 4%, and 2% $H_2SO_3$ (w/w) were freshly prepared in 500 mL bottles from sulfurous acid solution (≥6% $H_2SO_3$, from Sigma-Aldrich). The sulfurous acid solutions were added to the wheat straw in the reactors and the reactors were sealed immediately. Each reactor was cooked at the pretreatment temperature of 130° C., in a preheated autoclave, for the selected pretreatment time. The pretreatment time does not include the time for the autoclave to reach the pretreatment temperature (e.g., about 20 minutes). At the end of the pretreatment, the reactors were cooled in an ice bath. The contents of the pressure tubes (e.g., pretreated material) was removed, weighed, and combined in a sealable plastic bag. A portion of the pretreated material was removed for washing, to prepare a washed pretreatment sample.

All experiments conducted with or based on $SO_2$/sulfurous acid were carried out in a fume hood, including the drying of samples for determining the dissolved solids and total solids concentrations.

The total amount of $SO_2$ available for pretreatment, as calculated for various pretreatments is shown below. In each case, the consistency of the slurry to be pretreated was about 10 wt %.

TABLE 1

Pretreatment conditions for various low temperature $SO_2$ pretreatments

| Mass of dry biomass (g) | Concentration of $H_2SO_3$ (w/w %) (about 52 mL) | Total amount of $SO_2$ (wt % based on dry weight of lignocellulosic biomass) | Initial pH | Pretreatment temperature (° C.) | Pretreatment time (min) |
|---|---|---|---|---|---|
| 6 | 2 | 14 | 1.47 | 130 | 180 |
| 6 | 4 | 28 | 1.26 | 130 | 180 |
| 6 | 6 | 42 | 1.13 | 130 | 180 |

In general, the pretreated wheat straw produced from the low temperature $SO_2$ pretreatments at 14, 28, and 42 wt % $SO_2$ (based on dry weight of lignocellulosic biomass) was found to visually resemble the non-treated material, albeit slightly darker. Even when the total amount of $SO_2$ was above 74 wt % (based on dry weight of lignocellulosic biomass), for a 60 minute cook at 130° C., the pretreated wheat straw, although somewhat broken down, resembled raw fiber, but darker. Notably, the low temperature $SO_2$ pretreatment produced a pretreated material that is easy to wash and/or filter. This pretreated material can be characterized by its freeness, which is a term that reflects the rate at which a dilute suspension of material (e.g., 3 g of pulp in 1 L of water) can be drained. The freeness, or drainage rate, which has been shown to be related to the surface conditions and swelling of the fibers, can be measured as Canadian Standard Freeness (CSF). Canadian Standard Freeness is determined by TAPPI Standard T-227 om-09, where higher numbers correspond to faster draining. For example, high quality wood pulp may have a CSF freeness of about 700 mL.

For comparative purposes, low temperature $H_2SO_4$ pretreatment of wheat straw was also conducted in pressure tube reactors (PT). The slurry, having an initial consistency of about 10 wt %, was prepared using 0.5 (w/w) % $H_2SO_4$, so that the total amount of $H_2SO_4$ was about 4.5 wt % based on dry weight of lignocellulosic biomass, the pretreatment temperature was 130° C., and the pretreatment time was 180 minutes. The pretreatment conditions for this low temperature $H_2SO_4$ pretreatment are shown in Table 2. Notably, the initial pH for the 4.5 wt % $H_2SO_4$ low temperature pretreatment and the 14 wt % $SO_2$ low temperature pretreatment were both 1.47.

TABLE 2

Pretreatment conditions for a low temperature $H_2SO_4$ pretreatment

| Mass of dry biomass (g) | Concentration of $H_2SO_4$ (w/w %) (about 52 mL) | Amount of $H_2SO_4$ (wt % based on dry weight of lignocellulosic biomass) | Initial pH | Pretreatment temperature (° C.) | Pretreatment time (min) |
|---|---|---|---|---|---|
| 6 | 0.5 | 4.5 | 1.47 | 130 | 180 |

The low temperature $SO_2$ pretreatment was also compared to a high temperature $SO_2$ pretreatment of wheat straw, conducted in a stainless steel tubular reactor. The pretreatment conditions are shown in Table 3, where the initial consistency was about 10%.

TABLE 3

Pretreatment conditions for a high temperature $SO_2$ pretreatment

| Mass of dry biomass (g) | Concentration of $H_2SO_3$ (w/w %) (about 13.5 mL) | Total amount of $SO_2$ (wt % based on dry weight of lignocellulosic biomass) | Initial pH | Pretreatment temperature (° C.) | Pretreatment time (min) |
|---|---|---|---|---|---|
| 1.5 | 3 | 21 | 1.4 | 230 | 3.7 |

The low temperature $SO_2$ pretreatment is also compared to a high temperature $H_2SO_4$ pretreatment of wheat straw, conducted in a steam gun. The pretreatment conditions are shown in Table 4. In this case, wheat straw was soaked overnight in a solution of $H_2SO_4$ having a pH of 1.4, and was pretreated at a consistency of 30%.

TABLE 4

Pretreatment conditions for a high temperature $H_2SO_4$ pretreatment

| Mass of dry biomass (g) | Concentration of $H_2SO_4$ (w/w %) | Amount of $H_2SO_4$ (wt % based on dry weight lignocellulosic biomass) | Initial pH | Pretreatment temperature (° C.) | Pretreatment time (min) |
|---|---|---|---|---|---|
| 240 | 0.54 | 1.26 | 1.4 | 200 | 2 |

Example 2: Analysis of Pretreated Material

A portion of the pretreated material was reserved for analysis.

Undissolved solids (UDS) concentration, total solids (TS) concentration, dissolved solids (DS) concentration, can be determined using methods accepted in the art. For example, UDS, TS, and DS are calculated according the methodology set out in Examples 3, 4, and 5 of U.S. Pat. No. 9,574,212, which is hereby incorporated by reference and particularly for the purpose of describing such methodology.

The concentration of monomeric sugars (e.g., concentration of glucose and/or xylose) in the $SO_2$ pretreated material can be determined using high performance liquid chromatography (HPLC). For example, the concentration of monomeric sugars such as xylose is calculated according the methodology set out in Example 6 of U.S. Pat. No. 9,574,212, which is hereby incorporated by reference and particularly for the purpose of describing such methodology.

The filtrate from a portion of the $SO_2$ pretreated material produced using the pretreatment conditions in the last row of Table 1, was found to contain 2.04 g/L glucose, 22.7 g/L xylose, and 0.04 g/L of furfural.

The carbohydrate content of the $SO_2$ pretreated material can be ascertained with a carbohydrate assay based on Determination of Structural Carbohydrates and Lignin in Biomass-LAP (Technical Report NREL/TP-510-42618). This assay can provide the cellulose content, xylan content, insoluble lignin content, and lignin content of the pretreated biomass, w/w on a dry basis. For example, the cellulose/glucan content, xylan content, and/or lignin content is determined using the methodology set out in Example 11 of U.S. Pat. No. 9,574,212, which is hereby incorporated by reference and particularly for the purpose of describing such methodology.

Figure 3:
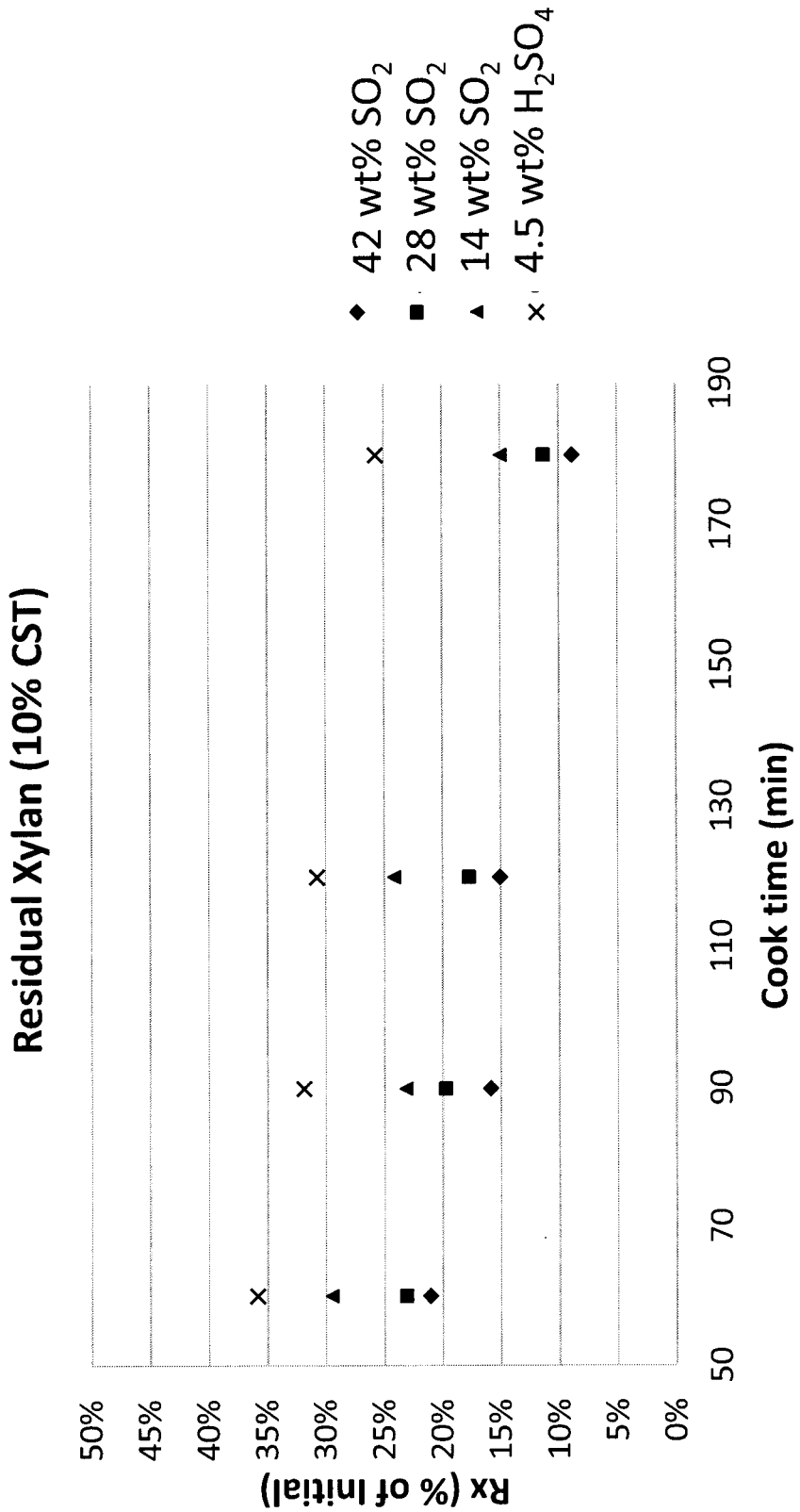
FIG. 3 is plot showing residual xylan as a function of pretreatment time.

The residual xylan and lignin dissolution provided by the SO$_2$ pretreatment is calculated relative to the untreated lignocellulosic biomass. The residual xylan for low temperature SO$_2$ pretreated wheat straw, where the pretreatment temperature was 130° C. and the consistency of the initial wheat straw slurry was 10 wt %, is shown in FIG. 3. Lignin dissolution for low temperature SO$_2$ pretreated wheat straw, where the pretreatment temperature was 130° C. and the consistency of the initial wheat straw slurry was 10 wt %, is shown in FIG. 4.

Referring to FIG. 3, residual xylan was found to be as low as about 10 wt % when the total amount of SO$_2$ is 28 or 42 wt %, based on dry weight of lignocellulosic biomass, and the cooking time is at least 180 minutes. Increasing severity by extending the pretreatment time to 360 minutes (not shown) reduces the residual xylan to less than 5%. Advantageously, the concentration of xylose produced during the pretreatment has been found to be relatively stable up to about 3.5 hours of pretreatment (e.g., with over 80%) recovery. Notably, the low temperature SO$_2$ pretreatment where the total amount of SO$_2$ is 14 wt % dry lignocellulosic biomass resulted in lower residual xylan than the low temperature H$_2$SO$_4$ pretreatment where the amount of H$_2$SO$_4$ is 4.5 wt % based on dry weight of lignocellulosic biomass.

Figure 4:
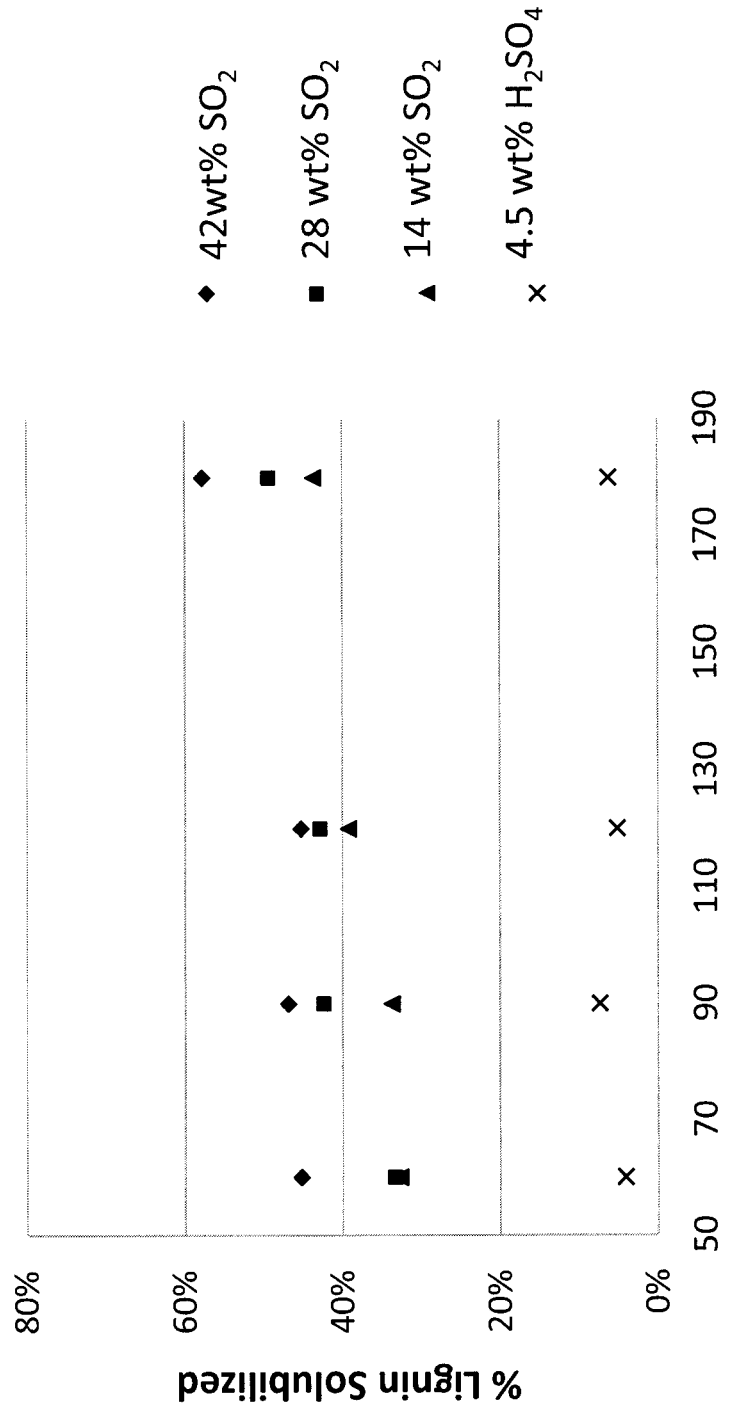
FIG. 4 is plot showing lignin dissolution as a function of pretreatment time.

Referring to FIG. 4, lignin dissolution is very good for the low temperature SO$_2$ pretreatment, but not good for the low temperature H$_2$SO$_4$ pretreatment. Remarkably, lignin dissolution reached or exceeded about 50% at the higher pretreatment times and SO$_2$ concentrations, without having to use added alkali and/or organic solvent.

Example 3: Enzymatic Hydrolysis

Washed pretreatment samples were prepared by suspending a portion of pretreated sample in ultra-purified water (Milli-Q™), filtering the suspension through glass fiber filter paper (G6, 1.6 microns), and then repeating the alternating steps.

The washed pretreatment solids were hydrolyzed in 50 mL Erlenmeyer flasks, at a consistency of about 10 wt %, with sodium citrate (1 M of citrate buffer pH added to a final concentration of 0.1M). The flasks were incubated at 52° C., with moderate shaking at about 250 rpm, for 30 minutes to equilibrate substrate temperature.

Hydrolysis was initiated by adding liquid cellulase enzyme. Enzyme was added at a dosage of 5 mg/g (i.e., mg protein/g of cellulose). The flasks were incubated at 52° C. in an orbital shaker (250 rpm) for various hydrolysis times (e.g., 200 hours).

The hydrolyses were followed by measuring the sugar monomers in the hydrolysate. More specifically, aliquots obtained at various hours of hydrolysis, were used to analyze the sugar content. Each aliquot was obtained at the specific time interval by swirling the flask, withdrawing 700 µL of the flask contents with a wide-bore pipette tip and depositing it in a 1.5 mL Eppendorf centrifuge tube, placing the centrifuge tube in a heating block for 10 minutes to deactivate the enzyme, and storing the aliquot at about 4° C. for subsequent sugar analysis.

To assay samples for monomeric sugars, the samples were warmed to room temperature and were centrifuged for 4 minutes at 14,800 rpm. The supernatant was diluted in water for measuring the glucose with HPLC.

The HPLC measured amount of glucose was used to determine the cellulose conversion. The cellulose conversion, which is expressed as the amount of glucose released during enzymatic hydrolysis of the solid fraction, and thus is referred to as glucose conversion, was determined using the following equation and the methodology outlined in Example 9 of U.S. Pat. No. 9,574,212, which is hereby incorporated by reference and particularly for the purpose of describing such methodology:

Cellulose Conversion=Concentration of Glucose in Aliquot/Maximum Glucose.

Figure 5:
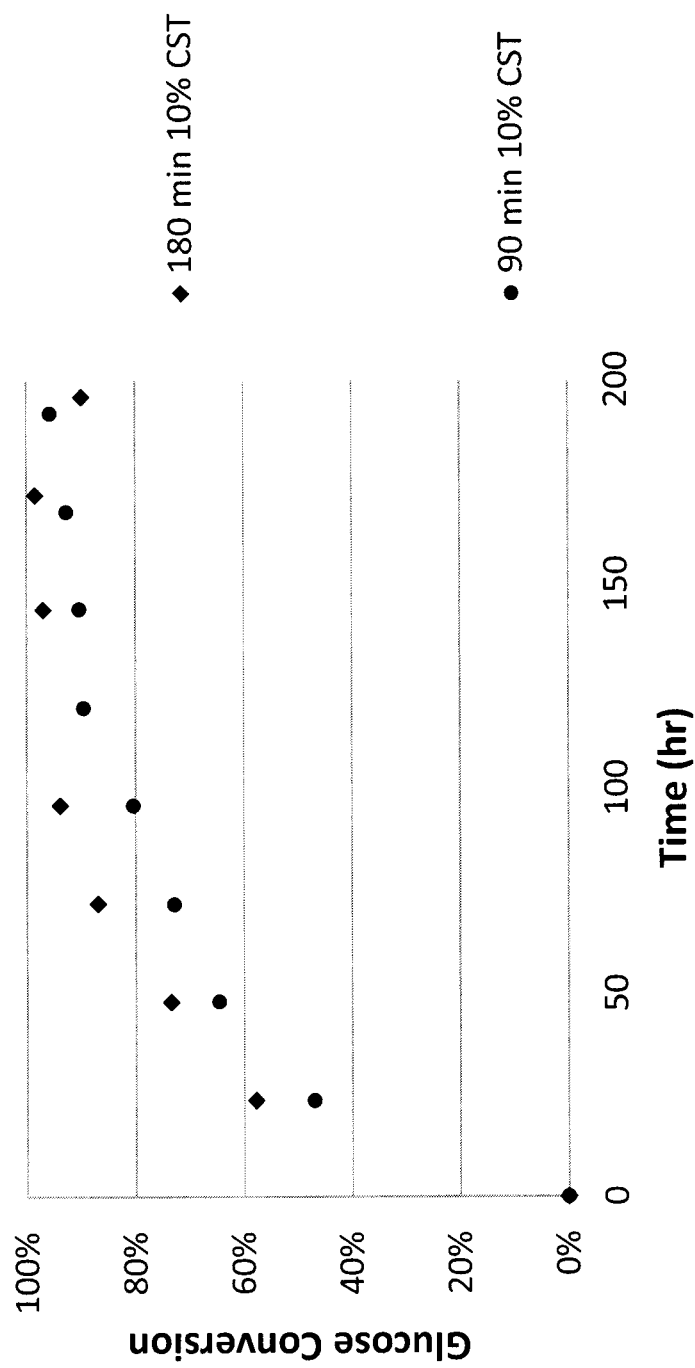
FIG. 5 is a plot of glucose conversion versus hydrolysis time for enzymatic hydrolysis of wheat straw subjected to a $SO_2$ pretreatment at 130° C. for 90 minutes and 180 minutes.
Figure 6:
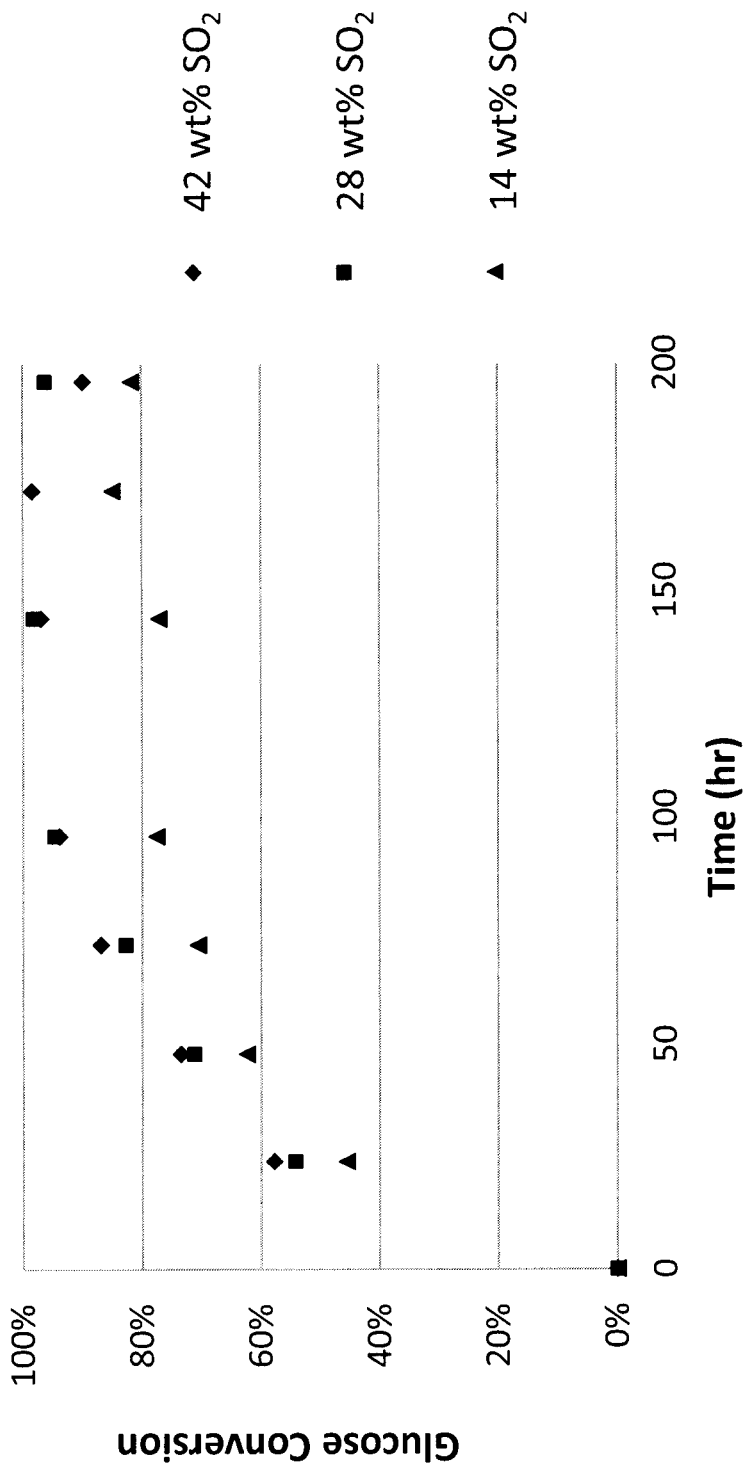
FIG. 6 is a plot of glucose conversion versus hydrolysis time for enzymatic hydrolysis of wheat straw subjected to a $SO_2$ pretreatment at 130° C. for 180 minutes with different total amounts of $SO_2$.

FIG. 5 shows a plot of glucose conversion for the washed solids of a SO$_2$ pretreatment conducted at 130° C. and 10% consistency, where the total amount of SO$_2$ is 42 wt %, based on dry weight of lignocellulosic biomass. Although, the pretreatments conducted for 90 minutes and 180 minutes both eventually reached more than 80% conversion, the pretreatment conducted for 180 minutes is significantly better. In particular, after only 72 hours of hydrolysis, the 180 minute pretreatment produced a glucose yield of about 87%, which is a significant improvement over the approximately 73% produced by the 90 minute pretreatment. After 96 hours of hydrolysis, the 180 minute pretreatment produced a glucose yield of about 94%, compared to the approximately 80% produced by the 90 minute pretreatment. Accordingly, the latter 90 minutes of pretreatment may be important for improving glucose yield (e.g., when the total amount of SO$_2$ is 42 wt % based on dry weight of lignocellulosic biomass). More specifically, it has been observed that when the total amount of SO$_2$ is 42 wt %, and the pretreatment is conducted at 130° C., there is a decent improvement for hydrolyses conducted on wheat straw pretreated for more than 120 minutes. FIG. 6 shows a plot of glucose conversion for the washed solids of a SO$_2$ pretreatment conducted at 130° C. and 10% consistency, for 180 minutes, where the total amount of SO$_2$ is varied between 42 wt %, 28 wt %, and 14 wt % (e.g., see Table 1). Although, the pretreatments conducted with a total amount of SO$_2$ that is 42 wt %, 28 wt %, and 14 wt %, eventually reach more than 80% conversion, the pretreatments conducted with a total amount of SO$_2$ that is 42 wt % or 28 wt %, is significantly better and/or more efficient.

In general, an efficient hydrolysis may exploit a relatively high glucose conversion, use less enzyme, and/or have shorter hydrolysis times. Referring to FIG. 6, the higher enzymatic efficiency resulting from low temperature SO$_2$ pretreatments conducted with a total amount of SO$_2$ is greater than or equal to about 28 wt % based on dry weight of lignocellulosic biomass, is demonstrated by the higher glucose conversion. For example, after only 72 hours of hydrolysis, the 42 wt % and 28 wt % SO$_2$ pretreatments resulted in a glucose yield greater than about 87% and 83%, respectively, which is a significant improvement over the approximately 71% resulting from the 14 wt % SO$_2$ pretreatment. In addition, after 96 hours of hydrolysis, the 42 wt % and 28 wt % SO$_2$ pretreatments produced a glucose yield greater than about 94%, compared to the 78% produced by the 14 wt % SO$_2$ pretreatment.

Figure 7:
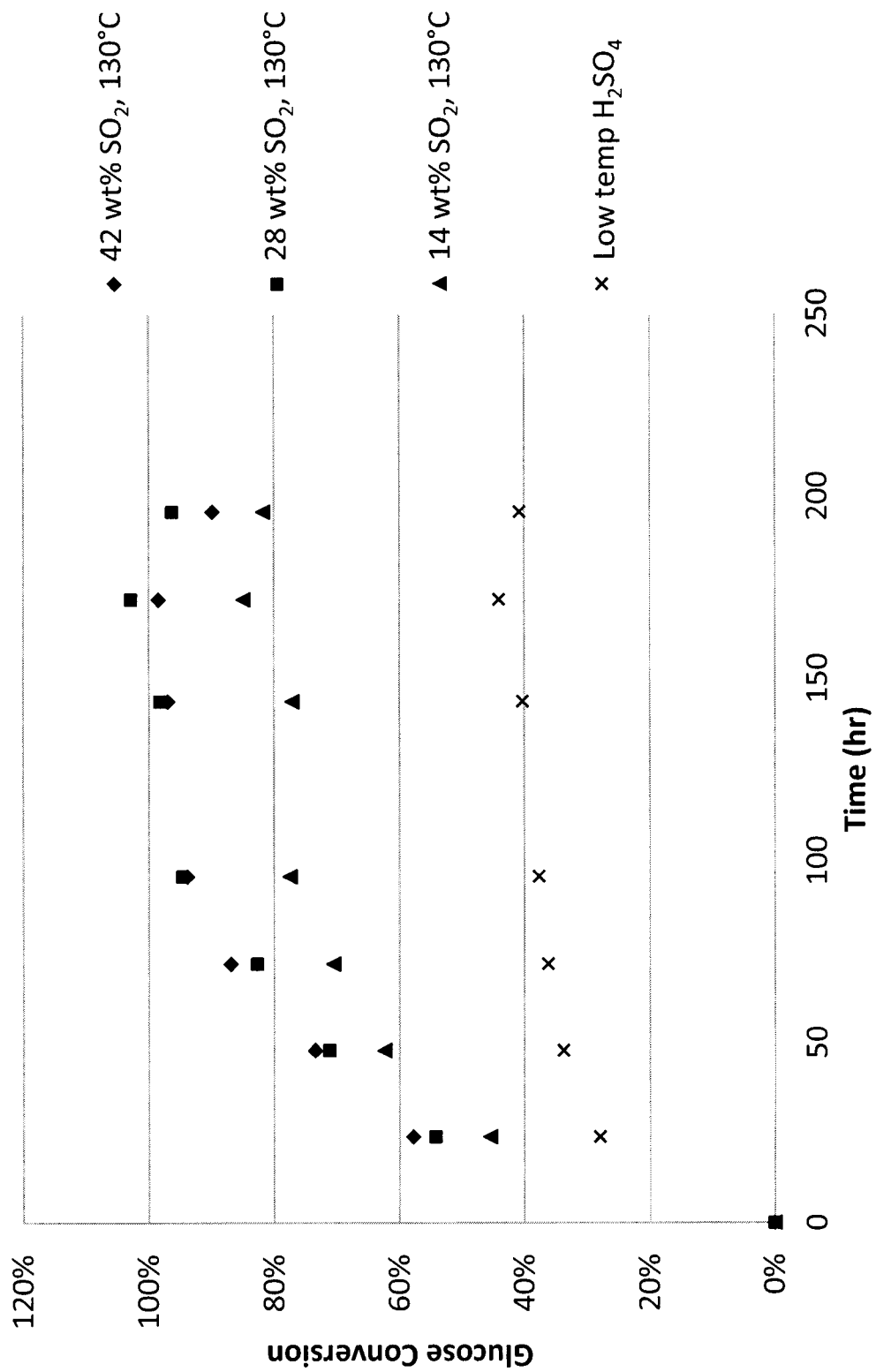
FIG. 7 shows the conversions illustrated in FIG. 6 relative to the glucose conversion of wheat straw subjected to a low temperature $H_2SO_4$ pretreatment (i.e., at 130° C. for 180 minutes)

FIG. 7 shows the cellulose conversions for the washed solids of the low temperature SO$_2$ pretreatments illustrated in FIG. 6, relative to the cellulose conversion for the washed solids of the low temperature H$_2$SO$_4$ pretreatment (i.e., conducted at 130° C., 10% consistency, for 180 minutes, 4.5 wt % H$_2$SO$_4$ based on dry weight of lignocellulosic biomass, as per Table 2), which was also conducted in a pressure tube. Notably, the low temperature SO$_2$ pretreatments are much more efficient than the low temperature H$_2$SO$_4$ pretreatment. For example, although the low temperature pretreatments using 4.5 wt % H$_2$SO$_4$ and 14 wt % SO$_2$, based on dry weight of lignocellulosic biomass, both had a similar initial pH, the low temperature $SO_2$ pretreatment had a glucose yield that was approximately doubled after 96 hours of hydrolysis, relative to the low temperature $H_2SO_4$ pretreatment. Moreover, for wheat straw, the low temperature $SO_2$ pretreatment has been found to require about ¼ of the enzyme to produce the same cellulose conversion as the low temperature $H_2SO_4$ pretreatment.

Figure 8:
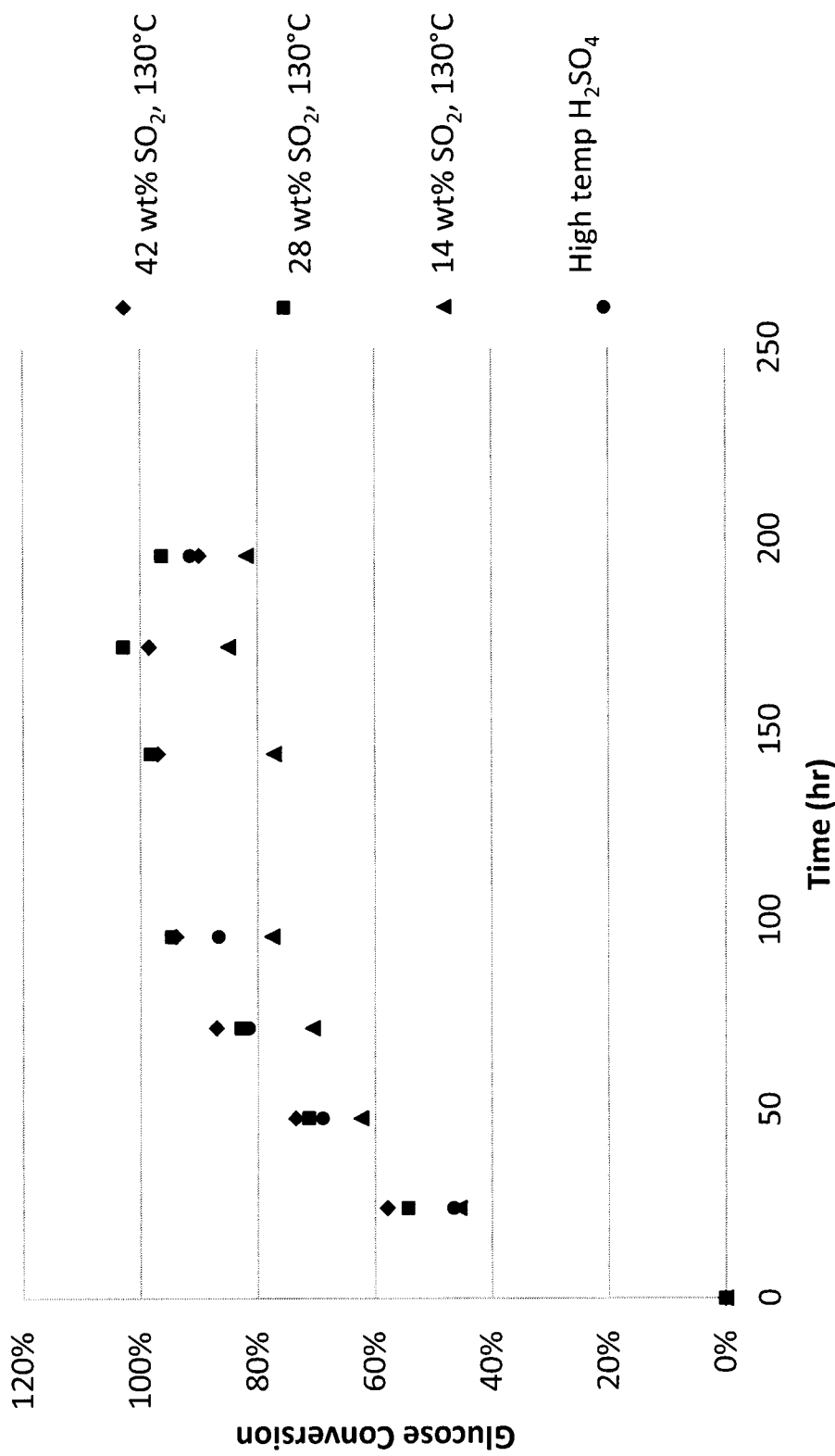
FIG. 8 shows the conversions illustrated in FIG. 6 relative to the glucose conversion of wheat straw subjected to a high temperature $H_2SO_4$ pretreatment (i.e., at 200° C. for 2 minutes)

FIG. 8 shows the cellulose conversions for the washed solids of the low temperature $SO_2$ pretreatments illustrated in FIG. 6, relative to the washed solids of a high temperature $H_2SO_4$ pretreatment (i.e., conducted at 200° C., 30% consistency, for 2 minutes, as per Table 4), which was conducted in a steam gun. Notably, this high temperature $H_2SO_4$ pretreatment, the conditions of which were previously optimized, is representative of a good $H_2SO_4$-catalyzed steam pretreatment. As evident from the graph, the low temperature $SO_2$ pretreatment, with high amounts of $SO_2$, was able to produce a higher cellulose conversion than the high temperature $H_2SO_4$ steam explosion pretreatment.

Figure 9:
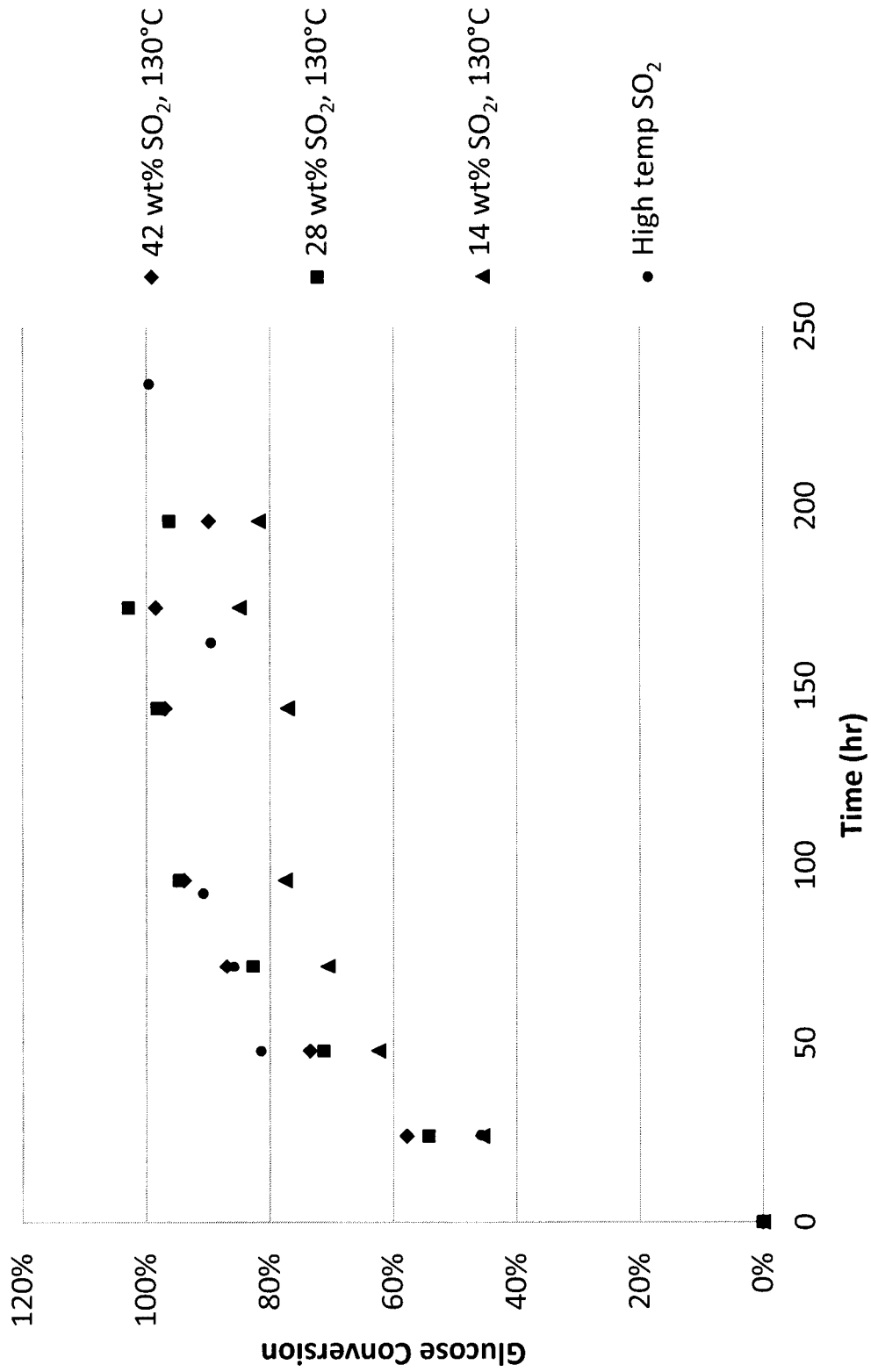
FIG. 9 shows the conversions illustrated in FIG. 6 relative to the glucose conversion of wheat straw subjected to a high temperature $SO_2$ pretreatment (i.e., at 230° C. for 3.7 minutes)

FIG. 9 shows the cellulose conversion for the washed solids of the low temperature $SO_2$ pretreatments illustrated in FIG. 6, relative to the washed solids of a high temperature $SO_2$ pretreatment (i.e., conducted at 230° C., 10% consistency, for 3.7 minutes, 21 wt % $SO_2$ based on dry weight of lignocellulosic biomass, as per Table 3), which was conducted in a stainless steel tubular reactor. As described in U.S. Pat. No. 9,574,212, high temperature $SO_2$ pretreatment can be more efficient than high temperature $H_2SO_4$ pretreatment. Surprisingly, the low temperature $SO_2$ pretreatment was able to produce a glucose conversion similar to that provided the high temperature $SO_2$ pretreatment, when the total amount of $SO_2$ at low temperature is at least 28 wt % based on dry weight of lignocellulosic biomass.

Figure 10:
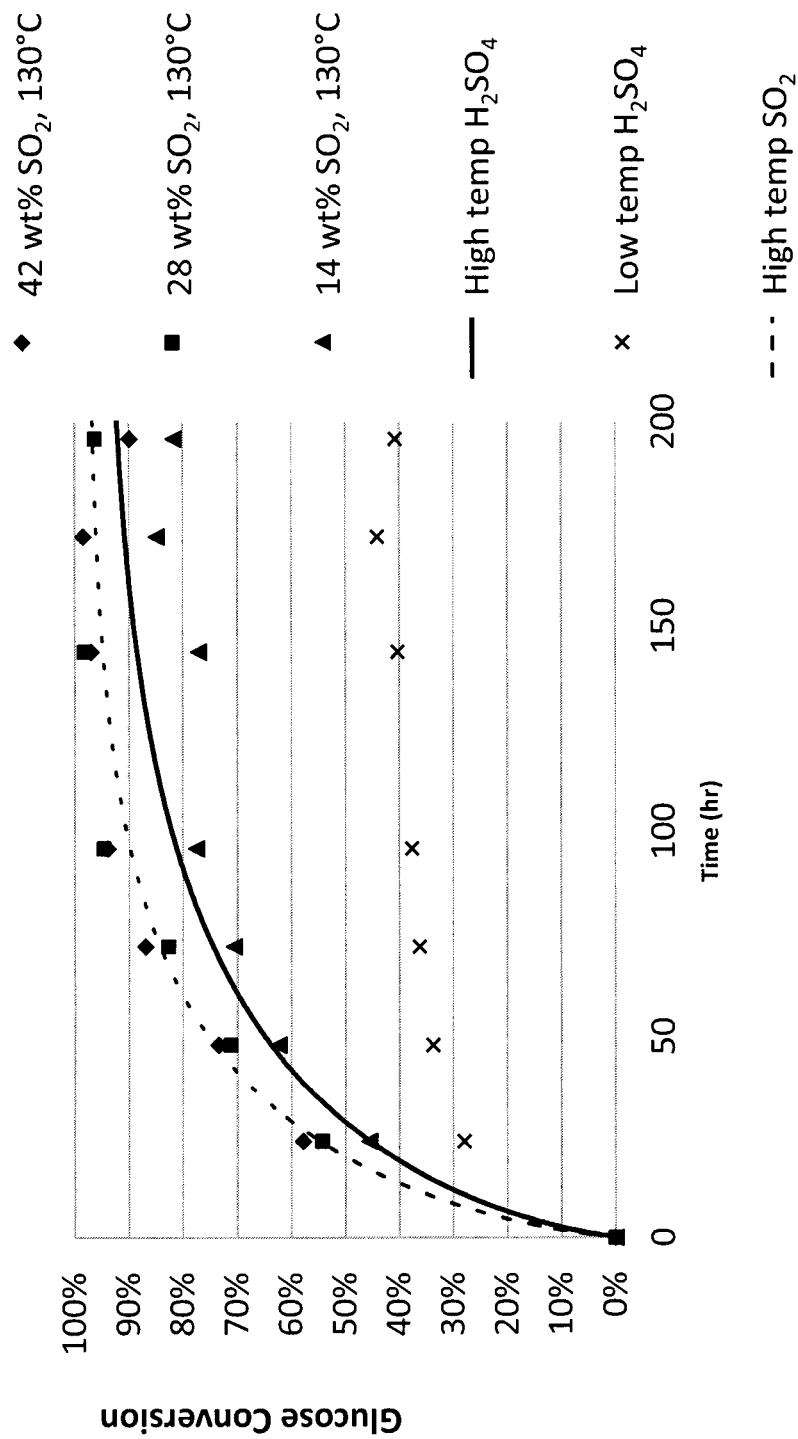
FIG. 10 provides a comparison of the conversions illustrated in FIG. 6 relative to the glucose conversions of wheat straw subjected to the high temperature pretreatments, where the latter are provided as curves generated from the data.

FIG. 10 shows the cellulose conversion for the washed solids of the low temperature $SO_2$ pretreatments illustrated in FIG. 6, relative to the washed solids of the high temperature $H_2SO_4$ and $SO_2$ pretreatments, illustrated in FIGS. 8 and 9 respectively, where the data is fit by non-linear regression. Referring to FIG. 10, the glucose conversion achieved when the wheat straw is pretreated with a total amount of $SO_2$ greater than or equal to about 28 wt % based on dry weight of lignocellulosic biomass is greater than that achieved by the high temperature $H_2SO_4$ pretreatment, and similar to that achieved by the high temperature $SO_2$ pretreatment. Advantageously, this efficiency is achieved without having to use high temperature pretreatment and/or the equipment associated therewith. Moreover, since xylose is relatively stable at these low temperature pretreatment conditions, the xylose yield may be larger and/or the concentration of potential inhibitors may be relatively low. For example, wheat straw pretreated at 130° C. with a total amount of $SO_2$ equal to about 42 wt % based on dry weight of lignocellulosic biomass (e.g., see Table 1) was found to contain <0.1 g/L of furfural, whereas wheat straw pretreated at 230° C. with a total amount of $SO_2$ equal to about 21 wt % based on dry weight of lignocellulosic biomass (e.g., see Table 3) was found to contain about 0.9 g/L of furfural.

Remarkably, these improvements are provided without having to add solvent, alkali, or carbonyl compounds. Accordingly, both capital and operating costs are lower, and $SO_2$ recovery is simplified.

Of course, the above embodiments have been provided as examples only. It will be appreciated by those of ordinary skill in the art that various modifications, alternate configurations, and/or equivalents will be employed without departing from the spirit and scope of the invention. Accordingly, the scope of the invention is therefore intended to be limited solely by the scope of the appended claims.

The invention claimed is:

1. A method for converting lignocellulosic biomass to glucose comprising:
   pretreating the lignocellulosic biomass to provide a pretreated material, said pretreating comprising subjecting the lignocellulosic biomass to a $SO_2$ pretreatment, said $SO_2$ pretreatment comprising heating said lignocellulosic biomass with at least one of sulfur dioxide and sulfurous acid, said heating conducted between 110° C. and 150° C. for more than 90 minutes, said $SO_2$ pretreatment conducted with a total amount of sulfur dioxide greater than 20 wt % based on dry weight of lignocellulosic biomass; and
   hydrolyzing at least 60% of the cellulose in the pretreated material to glucose, said hydrolyzing including adding enzyme to at least a solid fraction of the pretreated material, said enzyme including a cellulase.

2. The method according to claim 1, wherein said hydrolyzing provides a cellulose conversion of at least 80% within 72 hours.

3. The method according to claim 2, wherein said pretreating does not include heating the lignocellulosic biomass above 150° C.

4. The method according to claim 2, wherein said heating is conducted above 120° C. for more than 100 minutes.

5. The method according to claim 4, wherein said heating is conducted for more than 120 minutes.

6. The method according to claim 5, wherein said heating is conducted for more than 180 minutes.

7. The method according to claim 2, wherein said heating is conducted between 125° C. and 135° C.

8. The method according to claim 1, wherein the total amount of sulfur dioxide is greater than 25 wt % based on dry weight of lignocellulosic biomass.

9. The method according to claim 1, wherein the total amount of sulfur dioxide is greater than 30 wt % based on dry weight of lignocellulosic biomass.

10. The method according to claim 1, wherein the total amount of sulfur dioxide is greater than 40 wt % based on dry weight of lignocellulosic biomass.

11. A method for converting lignocellulosic biomass to glucose comprising:
    pretreating the lignocellulosic biomass to provide a pretreated material, said pretreating comprising subjecting the lignocellulosic biomass to a $SO_2$ pretreatment, said $SO_2$ pretreatment comprising heating said lignocellulosic biomass with at least one of sulfur dioxide and sulfurous acid, said heating conducted between 110° C. and 150° C. for more than 90 minutes; and
    hydrolyzing at least 60% of the cellulose in the pretreated material to glucose, said hydrolyzing including adding enzyme to at least a solid fraction of the pretreated material, said enzyme including a cellulase,
    wherein said $SO_2$ pretreatment is conducted with a total amount of sulfur dioxide greater than 70 wt % based on dry weight of lignocellulosic biomass.

12. The method according to claim 6, wherein the total amount of sulfur dioxide is between 20 wt % and 60 wt % based on dry weight of lignocellulosic biomass.

13. The method according to claim 2, wherein the lignocellulosic biomass comprises at least one of wheat straw and sugar cane bagasse.

14. The method according claim 2, wherein said adding enzyme comprises adding cellulase at a dosage of less than about 12 milligrams protein per gram of cellulose.

15. The method according to claim 2, wherein the total amount of sulfur dioxide is sufficient to provide an initial pH less than 1.25.

16. The method according to claim 2, wherein the total amount of sulfur dioxide is sufficient to provide an initial pH less than 1.

17. A method for converting lignocellulosic biomass to glucose comprising:
pretreating the lignocellulosic biomass to provide a pretreated material, said pretreating comprising subjecting the lignocellulosic biomass to a $SO_2$ pretreatment, said $SO_2$ pretreatment comprising heating said lignocellulosic biomass with at least one of sulfur dioxide and sulfurous acid, said heating conducted between 110° C. and 150° C. for more than 90 minutes, said $SO_2$ pretreatment conducted with a total amount of sulfur dioxide greater than 20 wt % based on dry weight of lignocellulosic biomass; and
hydrolyzing at least 60% of the cellulose in the pretreated material to glucose, said hydrolyzing including adding enzyme to at least a solid fraction of the pretreated material, said enzyme including a cellulase,
wherein said hydrolyzing provides a cellulose conversion of at least 80% within 72 hours, and
wherein said pretreating is conducted in the absence of added alkali.

18. A method for converting lignocellulosic biomass to glucose comprising:
pretreating the lignocellulosic biomass to provide a pretreated material, said pretreating comprising subjecting the lignocellulosic biomass to a $SO_2$ ; pretreatment, said $SO_2$ pretreatment comprising heating said lignocellulosic biomass with at least one of sulfur dioxide and sulfurous acid, said heating conducted between 110° C. and 150° C. for more than 90 minutes, said $SO_2$ pretreatment conducted with a total amount of sulfur dioxide greater than 20 wt % based on dry weight of lignocellulosic biomass; and
hydrolyzing at least 60% of the cellulose in the pretreated material to glucose, said hydrolyzing including adding enzyme to at least a solid fraction of the pretreated material, said enzyme including a cellulase,
wherein said hydrolyzing provides a cellulose conversion of at least 80% within 72 hours, and
wherein said pretreating is conducted in the absence of added organic solvent.

19. The method according to claim 2, wherein pretreating the lignocellulosic biomass to provide a pretreated material comprises pretreating lignocellulosic biomass having a consistency between 10 wt % and 40 wt %.

20. The method according to claim 2, comprising:
subjecting the pretreated material to a solid/liquid separation that provides a liquid fraction and the solid fraction, and
washing the solid fraction prior to said hydrolyzing.

21. A process for the production of an alcohol from lignocellulosic biomass, said process comprising:
feeding the lignocellulosic biomass into a pretreatment reactor;
pretreating the lignocellulosic biomass in the pretreatment reactor to provide a pretreated material, said pretreating comprising heating the lignocellulosic biomass with at least one of sulfur dioxide and sulfurous acid between 110° C. and 150° C. for more than 100 minutes, where a total amount of sulfur dioxide is greater than 20 wt % based on dry weight of lignocellulosic biomass, where alkali is added in an amount in the range from 0 to 0.5 wt % based on dry weight of incoming lignocellulosic biomass and organic solvent is added in an amount in the range from 0 to 5 wt % based on dry weight of incoming lignocellulosic biomass;
hydrolyzing at least 60% of the cellulose in the lignocellulosic biomass to glucose, said hydrolyzing including adding cellulase;
fermenting the glucose to produce the alcohol; and
recovering the alcohol.

* * * * *

UNITED STATES PATENT AND TRADEMARK OFFICE
CERTIFICATE OF CORRECTION

PATENT NO. : 11,299,850 B2
APPLICATION NO. : 16/761180
DATED : April 12, 2022
INVENTOR(S) : Brian Foody It is certified that error appears in the above-identified patent and that said Letters Patent is hereby corrected as shown below:

On the Title Page

On Page 3, Column 2, Line 50, under Other Publications, delete "Bioresour" and insert --Bioresource--.

On Page 3, Column 2, Line 64, under Other Publications, delete "Bioresouces," and insert --Bioresources,--.

On Page 4, Column 1, Line 23, under Other Publications, delete "lmpregnated" and insert --Impregnated--.

On Page 4, Column 2, Line 10, under Other Publications, delete "Celluloytic" and insert --Cellulolytic--.

On Page 5, Column 1, Line 64, under Other Publications, delete "(AVAR)" and insert --(AVARP)--.

In the Specification

In Column 7, Line 35, delete "$Ca^+$," and insert --$Ca^{2+}$,--.

In Column 7, Line 36, delete "$Mg^+$," and insert --$Mg^{2+}$,--.

In Column 19, Line 32, delete "Myceliopthora," and insert --Myceliophthora,--.

In the Claims

In Column 30, Claim 14, Line 65, after "according" insert --to--.

In Column 31, Claim 18, Line 31 (Approx.), delete "$SO_2$;" and insert --$SO_2$--.

Signed and Sealed this
Seventeenth Day of October, 2023

Katherine Kelly Vidal
*Director of the United States Patent and Trademark Office*